United States Patent
Conejo-Garcia et al.

(10) Patent No.: US 9,724,393 B2
(45) Date of Patent: Aug. 8, 2017

(54) METHOD FOR TREATMENT OF METASTATIC AND REFRACTORY CANCERS AND TUMORS WITH AN INDUCER THAT OVERCOMES INHIBITION OF T CELL PROLIFERATION

(71) Applicant: The Wistar Institute of Anatomy and Biology, Philadelphia, PA (US)

(72) Inventors: Jose R. Conejo-Garcia, Philadelphia, PA (US); Michael Allegrezza, Philadelphia, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 15/285,854

(22) Filed: Oct. 5, 2016

(65) Prior Publication Data
US 2017/0020964 A1 Jan. 26, 2017

Related U.S. Application Data

(60) Provisional application No. 62/237,746, filed on Oct. 6, 2015.

(51) Int. Cl.
| | |
|---|---|
| *A61P 35/00* | (2006.01) |
| *A61P 35/04* | (2006.01) |
| *A61K 38/20* | (2006.01) |
| *A61K 38/17* | (2006.01) |
| *A61K 31/519* | (2006.01) |
| *A61K 31/506* | (2006.01) |
| *A61K 31/397* | (2006.01) |
| *A61K 31/4184* | (2006.01) |
| *A61K 31/4458* | (2006.01) |
| *A61K 31/437* | (2006.01) |
| *A61K 31/145* | (2006.01) |
| *C07K 14/54* | (2006.01) |
| *C07K 14/715* | (2006.01) |
| *C07D 471/04* | (2006.01) |

(52) U.S. Cl.
CPC ........ *A61K 38/2086* (2013.01); *A61K 31/145* (2013.01); *A61K 31/397* (2013.01); *A61K 31/4184* (2013.01); *A61K 31/437* (2013.01); *A61K 31/4458* (2013.01); *A61K 31/506* (2013.01); *A61K 31/519* (2013.01); *A61K 38/1793* (2013.01); *A61K 38/2013* (2013.01); *A61K 38/2046* (2013.01); *C07D 471/04* (2013.01); *C07K 14/5418* (2013.01); *C07K 14/5443* (2013.01); *C07K 14/7155* (2013.01)

(58) Field of Classification Search
None
See application file for complete search history.

(56) References Cited

U.S. PATENT DOCUMENTS

| | | |
|---|---|---|
| 7,078,053 B2 | 7/2006 | Bunick et al. |
| 2014/0037579 A1 | 2/2014 | Cannon et al. |
| 2015/0359853 A1 | 12/2015 | Felber et al. |

FOREIGN PATENT DOCUMENTS

| | | |
|---|---|---|
| CA | 2923990 | 3/2015 |
| WO | WO-2009/002562 | 12/2008 |
| WO | WO-2014/066527 | 5/2014 |

OTHER PUBLICATIONS

Akinleye et al, 2013. Journal of Hematology & Oncology 6:27; pp. 1-11 as printed.*
Allegrazza et al (2016. Cancer Res. 76(9): 2561-2572).*
Lugowska et al, 2015. Oncotargets and Therapy. 8: 2251-2259.*
Hu-Lieskovan, 2015 (Mar. 18). Sci Transl med. 7(279): 1-11.*
On-line publication by DIGNA Biotech, "Improving IL-15 antitumor efficacy: fusion protein strategy".
MedChem Express (MCE), Cobimetinib.
MedChem Express (MCE), Cobimetinib (R-enantiomer).
MedChem Express (MCE), Selumetinib.
MedChem Express (MCE), Cobimetinib racemate.
MedChem Express (MCE), GDC-0623.
Xu, W. et al., Efficacy and mechanism-of-action of a novel superagonist interleukin-15: interleukin-15 receptor alphaSu/Fc fusion complex in syngeneic murine models of multiple myeloma, Cancer Research, May 2013, 73(10):3075-3086.
Vesely, M.D. et al., Natural innate and adaptive immunity to cancer, Annu Rev Immunol, Jan. 2011, 29:235-271.
Smith-Garvin, J. E. et al., T cell activation, Annu Rev Immunol, Jan. 2009, 27:591-619.
Miranda, M.B. et al., Signal transduction pathways that contribute to myeloid differentiation, Leukemia, Apr. 2007, 21:1363-1377.
Vella, L.J. et al., MEK inhibition, alone or in combination with BRAF inhibition, affects multiple functions of isolated normal human lymphocytes and dendritic cells, Cancer Immunol Research, Apr. 2014, 2(4): 351-60.
Boni, A. et al., Selective BRAFV600E inhibition enhances T-cell recognition of melanoma without affecting lymphocyte function, Cancer Research, Jul. 2010, 70(13): 5213-5219.
Yamaguchi, T. et al., Suppressive effect of an orally active MEK1/2 inhibitor in two different animal models for rheumatoid arthritis: a comparison with leflunomide, Inflammation Research, Jan. 2012, 61:445-454.

(Continued)

*Primary Examiner* — Zachary Howard
(74) *Attorney, Agent, or Firm* — Howson & Howson LLP

(57) ABSTRACT

A method of treating a mammalian subject with cancer comprises administering to said subject having a cancer, e.g., a metastatic or refractory cancer or tumor, a small molecule inhibitor of a target signaling molecule of the MEK/MAPK pathway that impairs T cell activation, and administering to said subject a molecule that induces T cell proliferation in the presence of said inhibitor. The combination of a small molecule inhibitor of a target of the MEK/MAPK pathway and the T cell proliferation inducer reduces the proliferation of the cancer and tumor cells in vivo. Compositions and kits including these components are also provided.

7 Claims, 29 Drawing Sheets

(56) References Cited

OTHER PUBLICATIONS

Liu, L.et al., The BRAF and MEK Inhibitors Dabrafenib and Trametinib: Effects on Immune Function and in Combination with Immunomodulatory Antibodies Targeting PD-1, PD-L1, and CTLA-4, Clinical Cancer Research, Apr. 2015, 21(7):1639-1651.
Kono, M. et al., Role of the mitogen-activated protein kinase signaling pathway in the regulation of human melanocytic antigen expression, Mol Cancer Res, Oct. 2006, 4(10):779-792.
Giachelli, C, M. et al., Evidence for a role of osteopontin in macrophage infiltration in response to pathological stimuli in vivo, American Journal of Pathology, Feb. 1998, 152(2):353-358.
Lin, C, N. et.al., the significance of the co-existence of osteopontin and tumor-associated macrophages in gastric cancer progression, BMC Cancer, Mar. 2015, 15:128.
Kim, E, K. et al., Tumor-derived osteopontin suppresses antitumor immunity by promoting extramedullary myelopoiesis, Cancer Research, Nov. 2014, 74(22):6705-6716.
Gao, N. et al., G1 cell cycle progression and the expression of G1 cyclins are regulated by PI3K/AKT/mTOR/p70S6K1 signaling in human ovarian cancer cells, AJP-Cell Physiol, Aug. 2004, 287:C281-C291.
Hou, J, Y. et al., Exploiting MEK inhibitor-mediated activation of ERalpha for therapeutic intervention in ER-positive ovarian carcinoma, PLoS One, Feb. 2013, 8(2):e54103.
Maus, M, V. et al., Ex vivo expansion of polyclonal and antigen-specific cytotoxic T lymphocytes by artificial APCs expressing ligands for the T-cell receptor, CD28 and 4-1BB, Nature Biotechnology, Feb. 2002, 20:143-148.
Stephen, T, L. et al., Transforming Growth Factor beta-Mediated Suppression of Antitumor T Cells Requires FoxP1 Transcription Factor Expression, Immunity, Sep. 2014, 41:4274-439.
Scarlett, U, K. et al., Ovarian cancer progression is controlled by phenotypic changes in dendritic cells, Journal of Experimental Medicine, Feb. 2012, 209(3):495-506.
Law, J, H. et al., Phosphorylated insulin-like growth factor-i/insulin receptor is present in all breast cancer subtypes and is related to poor survival, Cancer Research, Dec. 2008, 68(24):10238-10246.
Waldmann, T, A. The biology of interleukin-2 and interleukin-15: implications for cancer therapy and vaccine design, Nature Reviews Immunology, Aug. 2006, 6:595-601.
Liao, W. et al., Interleukin-2 at the crossroads of effector responses, tolerance, and immunotherapy, Immunity, Jan. 2013, 38:13-25.
Ueda, Y. et al., Protein kinase C activates the MEK-ERK pathway in a manner independent of Ras and dependent on Raf, Journal of Biological Chemistry, Sep. 1996, 271(38):23512-23519.
Huarte, E. et al., Depletion of dendritic cells delays ovarian cancer progression by boosting antitumor immunity, Cancer Research, Sep. 2008, 68(18):7684-7691.
Nesbeth, Y, C. et al., CD4+ T cells elicit host immune responses to MHC class II—ovarian cancer through CCL5 secretion and CD40-mediated licensing of dendritic cells, Journal of Immunology, Apr. 2010, 184(10):5654-5662.
Rutkowski, M, R. et al., Initiation of metastatic breast carcinoma by targeting of the ductal epithelium with adenovirus-cre: a novel transgenic mouse model of breast cancer, Journal of Visualized Experiments, Mar. 2014, 85:e51171.
Jackson, E, L. et al., Analysis of lung tumor initiation and progression using conditional expression of oncogenic K-ras, Genes & Development, Dec. 2001, 15(24):3243-8.
Jonkers, J. et al., Synergistic tumor suppressor activity of BRCA2 and p53 in a conditional mouse model for breast cancer, Nature Genetics, Dec. 2001, 29:418-25.
Wee, S. et al., PI3K pathway activation mediates resistance to MEK inhibitors in KRAS mutant cancers, Cancer Res, May 2009, 69:4286-93.
Mirzoeva, O, K. et al., Basal subtype and MAPK/ERK kinase (MEK)-phosphoinositide 3-kinase feedback signaling determine susceptibility of breast cancer cells to MEK inhibition, Cancer Res, Jan. 2009, 69(2):565-572.
Turke, A, B. et al., MEK inhibition leads to PI3K/AKT activation by relieving a negative feedback on ERBB receptors, Cancer Research, Jul. 2012, 72(13):3228-3237.
Marigo, I. et al., Tumor-induced tolerance and immune suppression depend on the C/EBPbeta transcription factor, Immunity, Jun. 2010, 32:790-802.
Bedard, P, L. et al., A phase Ib dose-escalation study of the oral pan-PI3K inhibitor buparlisib (BKM120) in combination with the oral MEK1/2 inhibitor trametinib (GSK1120212) in patients with selected advanced solid tumors, Clinical Cancer Research, Feb. 2015, 21(4):730-738.
Blumenschein, G, R, Jr. et al., A randomized phase II study of the MEK1/MEK2 inhibitor trametinib (GSK1120212) compared with docetaxel in KRAS-mutant advanced non-small-cell lung cancer (NSCLC)dagger, Annals of Oncology, May 2015, 26(5):894-901.
Engelman, J, A. et al., Effective use of PI3K and MEK inhibitors to treat mutant Kras G12D and PIK3CA H1047R murine lung cancers, Nature Medicine, Dec. 2008, 14(12):1351-1356.
Rutkowski, M, R. et al., Microbially driven TLR5-dependent signaling governs distal malignant progression through tumor-promoting inflammation, Cancer Cell, Jan. 2015, 27:27-40.
Roby, K, F. et al., Development of a syngeneic mouse model for events related to ovarian cancer, Carcinogenesis, Apr. 2000, 21(4):585-591.
Conejo-Garcia, J, R. et al., Tumor-infiltrating dendritic cell precursors recruited by a beta-defensin contribute to vasculogenesis under the influence of Vegf-A, Nature Medicine, Aug. 2004, 10(9):950-958.
Huarte, E. et al., PILAR is a novel modulator of human T-cell expansion, Blood, Aug. 2008, 112(4):1259-1268.
Cox, J. and Mann, M. MaxQuant enables high peptide identification rates, individualized p. p.b.-range mass accuracies and proteome-wide protein quantification, Nature Biotechnology, Nov. 2008, 26(12): 1367-1372.
Wu, J. Il-15 Agonists: The Cancer Cure Cytokine, J Mol Genet Med, Feb. 2014, 7:85.
Scarlett, U, K. et al., In situ stimulation of CD40 and Toll-like receptor 3 transforms ovarian cancer-infiltrating dendritic cells from immunosuppressive to immunostimulatory cells, Cancer Res, Sep. 2009, 69(18):7329-7337.
Zhu, X. et al., Novel Human Interleukin-15 Agonists, Journal of Immunology, Sep. 2009, 183(6):3598-3607.
Infante, J. R. et al., A phase lb study of trametinib, an oral Mitogen-activated protein kinase kinase (MEK) inhibitor, in combination with gemcitabine in advanced solid tumours, European Journal of Cancer, Jun. 2013, 49(9):2077-2085.
Cantley, L. C., The phosphoinositide 3-kinase pathway, Science, May 2002, 296:1655-1657.
Budagian, V. et al., IL-15/IL-15 receptor biology: a guided tour through an expanding universe, Cytokine Growth Factor Reviews, Aug. 2006, 17(4):259-280.
Huynh, H. et al., Targeted inhibition of the extracellular signal-regulated kinase kinase pathway with AZD6244 (ARRY-142886) in the treatment of hepatocellular carcinoma, Mol Cancer Ther, Jan. 2007, 6(1):138-146.
Hoeflich, K. P. et al., Intermittent Administration of MEK Inhibitor GDC-0973 plus PI3K Inhibitor GDC-0941 Triggers Robust Apoptosis and Tumor Growth Inhibition, Cancer Research, Jan. 2012, 72(1):210-219.
Hatzivassiliou, G. et al., Mechanism of MEK inhibition determines efficacy in mutant KRAS—versus BRAF-driven cancers, Nature, Sep. 2013, 501(7466):232-236.
International Search Report dated Dec. 16, 2016 in corresponding International Patent Application PCT/US16/55458, filed Oct. 5, 2016.
Written Opinion dated Dec. 16, 2016 in corresponding International Patent Application PCT/US16/55458, filed Oct. 5, 2016.

* cited by examiner

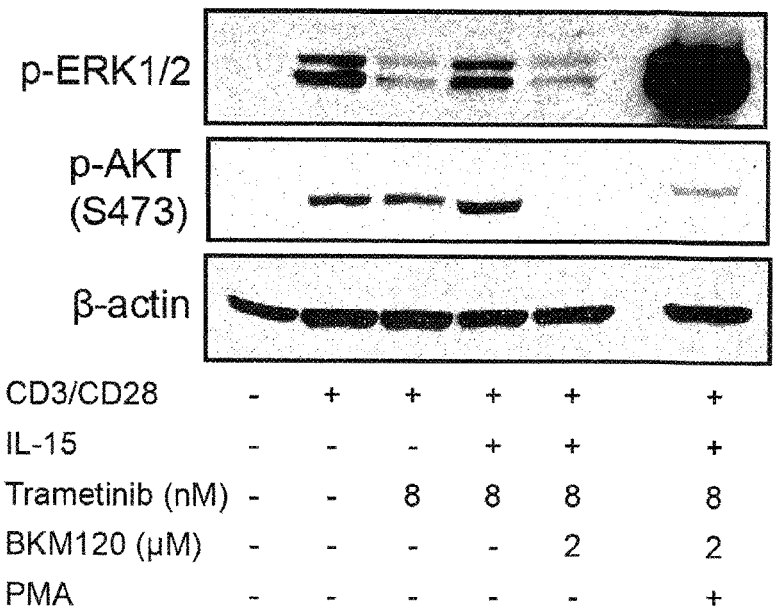
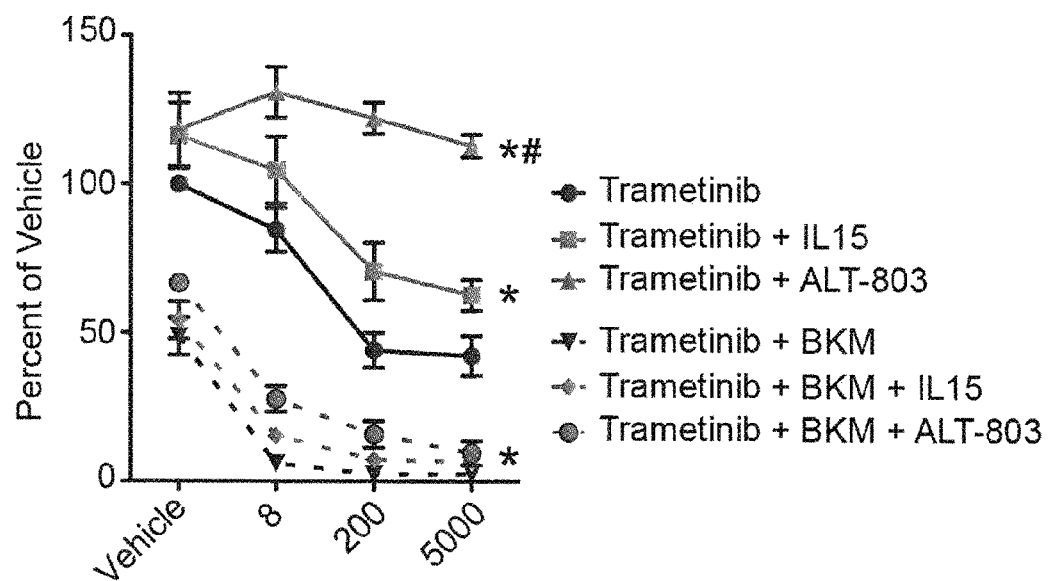

FIG. 10

| Cells Treated with: | % hPBMC that proliferate with GDC0973 relative to vehicle treatment with same cytokine after 7 days | |
|---|---|---|
| | CD4 | CD8 |
| ConA only | 4.3 | 3.4 |
| IL-2 | 50.2 | 37.0 |
| IL-7 | 41.3 | 34.9 |
| IL-15 | 38.9 | 53.9 |
| IL-21 | 4.5 | 4.6 |
| IL-27 | 4.3 | 5.7 |
| IL-2 + IL-7 | 75.6 | 76.4 |
| IL-2 + IL-15 | 61.3 | 72.7 |
| IL-2 + IL-21 | 50.3 | 47.3 |
| IL-2 + IL-27 | 57.5 | 55.9 |
| IL-7 + IL-15 | 75.2 | 84.6 |
| IL-7 + IL-21 | 49.2 | 56.4 |
| IL-7 + IL-27 | 48.9 | 31.7 |
| IL-15 + IL-21 | 51.0 | 69.7 |
| IL-15 + IL-27 | 57.2 | 78.7 |
| IL-21 + IL-27 | 7.9 | 8.2 |

US 9,724,393 B2

METHOD FOR TREATMENT OF METASTATIC AND REFRACTORY CANCERS AND TUMORS WITH AN INDUCER THAT OVERCOMES INHIBITION OF T CELL PROLIFERATION

CROSS-REFERENCE TO RELATED APPLICATIONS

This application claims the benefit of the priority of U.S. Provisional Patent Application No. 62/237,746 filed Oct. 6, 2015, which application is incorporated herein by reference.

STATEMENT REGARDING FEDERALLY SPONSORED RESEARCH OR DEVELOPMENT

This invention was made with government support under Grant Nos. P30 CA010815, R01 CA124515, R01 CA157664, R01 CA178687, and U54 CA151662 awarded by the National Institutes of Health. The government has certain rights in this invention.

BACKGROUND OF THE INVENTION

Small molecule kinase inhibitors have been rigorously tested to demonstrate their efficacy on tumor cells, but their effects on the interplay between leukocytes and tumors have been largely unstudied due to the use of preclinical xenograft models that lack a competent immune system. T cells, crucial for controlling the growth of immunogenic tumors[1], rely upon many of the same signaling pathways targeted by pharmaceutical inhibitors. For instance, engagement of the T cell receptor (TCR) and co-stimulatory receptors activates the Ras-MAPK (mitogen-activated protein kinase) and PI3K-AKT signaling cascades, which are necessary for proliferation and effector function in T cells[2]. Additionally, the development of myeloid leukocytes also depends upon these pathways[3].

The FDA-approved small molecule MEK1/2 inhibitor trametinib represents an example of seemingly paradoxical interactions with host anti-tumor immunity. Studies have shown that proper T cell activation and proliferation are impaired by pharmacological inhibition of MEK signaling, both with trametinib[4,5] and other compounds[6]. These data imply that trametinib would impair anti-tumor T cell function in tumor hosts. However, it was recently found that while trametinib impairs T cell function in vitro, it does not limit the effectiveness of either adoptive cell therapy[7] or checkpoint blockade with antibodies against PD-1, PD-L1, and CTLA-4[7] in mouse models. In fact, in these studies trametinib was able to synergize with immunomodulatory therapies. Additionally, MEK inhibition of tumor cells can lead to increased expression of tumor antigens[6,9].

There remains a need in the art for new and effective tools to facilitate treatment of metastatic and refractory cancers and tumors.

SUMMARY OF THE INVENTION

In one aspect, a method of treating a mammalian subject with cancer comprises (a) administering to said subject having a metastatic or refractory cancer or tumor a small molecule kinase inhibitor of a target enzyme in the MEK/MAPK pathway; and (b) administering to said subject a molecule that induces T cell proliferation in the presence of said inhibitor. The combination of (a) and (b) reduces the proliferation of said cancer and tumor cells in vivo.

In another aspect, a composition or kit for treatment of a mammalian subject with a metastatic or refractory cancer or tumor comprises (a) an effective amount of a small molecule kinase inhibitor of a target enzyme in the MEK/MAPK pathway and (b) an effective amount of a molecule that induces T cell proliferation in the presence of said inhibitor. The components (a) and (b) are formulated with a pharmaceutically acceptable carrier or diluent.

Still other aspects and advantages of these compositions and methods are described further in the following detailed description of the preferred embodiments thereof.

BRIEF DESCRIPTION OF THE DRAWINGS

FIG. 2C is a blot showing FACS-sorted human CD8 T cells that were stimulated by anti-CD3/CD28 crosslinking in the presence of the indicated compounds as described in methods. After 10 min, cells were harvested for Western blotting.

FIG. 2D is a graph showing that human PBMCs were activated as in FIG. 2B with the indicated compounds, BKM120=2 μM. Division index of CD8 T cells as percent of vehicle alone is shown as means from 3 different donors. *=P<0.05 compared to trametinib 5000 nM, #=P<0.05 compared to trametinib 5000 nM+IL-15.

FIG. 10 is a table that illustrates that IL-15, IL-2, and IL-7 can rescue T cell proliferation from MEK inhibition. Human PBMCs were stained with CELLTRACE reagent and activated with ConA in the presence of vehicle or GDC0973 (1.45 μM) and the indicated cytokines (IL-2=20 U/ml, IL-7=2 ng/ml, IL-15=10 ng/ml, IL-21=100 ng/ml, IL-27=50 ng/ml). Reported are percentages of cells that proliferated with GDC0973 relative to vehicle treatment with the same cytokines after 7 days. Stains are not depicted.

DETAILED DESCRIPTION

Figure 1A:
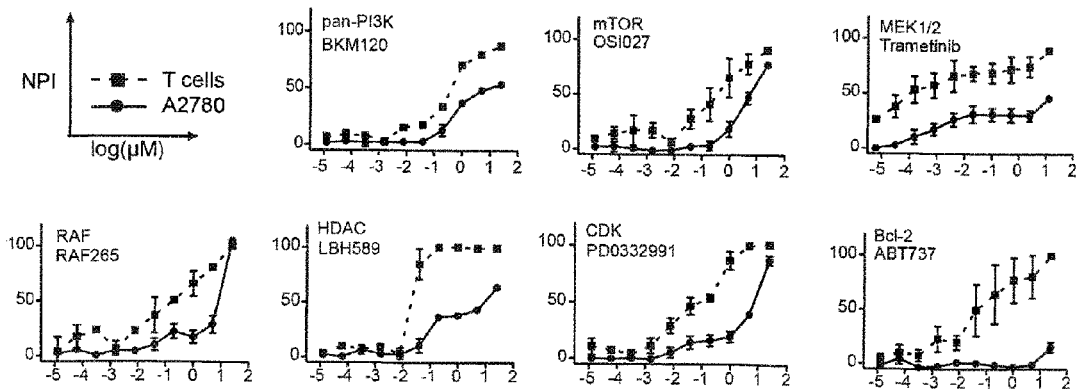
FIG. 1A shows eight plots of targeted small molecule inhibitors that suppress T cell responses in vitro. A2780 cells were cultured for 3 days and human T cells were activated with Concanavalin A (ConA) for 7 days in the indicated compounds, BKM120, OSI127, Trametrinib, RAF, LBH589 and PD0332991 and ABT747. Plots show the normalized percent inhibition (NPI) vs. concentration in log (μM).

The methods and compositions described herein involve the observation that common enzyme pathway inhibitors, preferably kinase inhibitors or inhibitors targeting multiple signaling molecules, e.g., inhibitors of target molecules or enzymes in the MEK/MAPK pathway, impair T cell activation at their active concentrations on cancer cells. Because T cell activation is necessary for control of cancer cell growth, spread and tumor reduction, such suppressive effects on T cell activation are not desirable in a cancer therapy or therapeutic. These effects, however, are overcome by the signaling of a proliferative cytokine, e.g., IL-15, IL-2 or IL-7, through PI3K activation, which synergizes with a signaling molecule inhibitor to elicit durable tumor rejection, resistant to tumor re-challenge.

Paradoxically, some signaling molecule inhibitors require the presence of CD8 T cells for tumor suppression, and are largely independent of direct inhibition of tumor cell proliferation. In one embodiment, the MEK inhibitor, trametinib, impairs the mobilization of Ly6C$^+$ Myeloid-Derived Suppressor Cells (MDSCs) from myeloid precursors, and also abrogates the production of MDSC-chemotactic osteopontin by tumor cells. These combined effects reduce MDSC accumulation at tumor beds, enhancing T cell-mediated protection.

As demonstrated in the examples below, the inventors have shown that the combined anti-inflammatory activity of trametinib on multiple cell types, irrespective of the tumor cell cycle, could be responsible for its anti-tumor effects. The inventors have identified an explanation for the effect of such inhibitors, e.g., MEK inhibitors, on MDSCs and thus provide methods and compositions to overcome the suppressive effects of inhibitors of signaling molecule pathways on T cells in the treatment of cancers, including refractory cancers.

A method of treating a mammalian subject with cancer comprises, in one aspect, administering to the subject having a cancer, including a metastatic or refractory cancer or tumor, a combination therapy. The combination therapy involves administering a small molecule kinase inhibitor of a target enzyme of the MEK/MAPK pathway and a molecule that induces T cell proliferation in the presence of the inhibitor. The combination of components (a) and (b) reduce the proliferation of the cancer and tumor cells in vivo. In another aspect, compositions or kits containing components (a) and (b) are further described herein for use in the treatment of cancer.

Components of the Methods and Compositions and Other Definitions

Technical and scientific terms used herein have the same meaning as commonly understood by one of ordinary skill in the art to which this invention belongs and by reference to published texts, which provide one skilled in the art with a general guide to many of the terms used in the present application. The following definitions are provided for clarity only and are not intended to limit the claimed invention.

The terms "a" or "an" refers to one or more, for example, "an inhibitor" is understood to represent one or more such compounds, molecules, peptides or antibodies. As such, the terms "a" (or "an"), "one or more," and "at least one" are used interchangeably herein.

As used herein, the term "about" means a variability of plus or minus 10% from the reference given, unless otherwise specified.

The words "comprise", "comprises", and "comprising" are to be interpreted inclusively rather than exclusively, i.e., to include other unspecified components or process steps. The words "consist", "consisting", and its variants, are to be interpreted exclusively, rather than inclusively, i.e., to exclude components or steps not specifically recited.

As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, and others.

The term "neoplastic disease", "cancer" or "proliferative disease" as used herein refers to any disease, condition, trait, genotype or phenotype characterized by unregulated or abnormal cell growth, proliferation or replication. A "cancer cell" is a cell that divides and reproduces abnormally with uncontrolled growth. This cell can break away from the site of its origin (e.g., a tumor) and travel to other parts of the body and set up another site (e.g., another tumor), in a process referred to as metastasis. A "tumor" is an abnormal mass of tissue that results from excessive cell division that is uncontrolled and progressive, and is also referred to as a neoplasm. Tumors can be either benign (not cancerous) or malignant. The abnormal proliferation of cells may result in a localized lump or tumor, be present in the lymphatic system, or may be systemic. In one embodiment, the neoplastic disease is benign. In another embodiment, the neoplastic disease is pre-malignant, i.e., potentially malignant neoplastic disease. In a further embodiment, the neoplastic disease is malignant, i.e., cancer. In still a further embodiment the neoplastic disease is a refractory cancer, i.e., a cancer or tumor that does not respond to treatment, such as surgery, radiation or chemotherapy. The cancer or tumor may be resistant at the beginning of treatment or it may become resistant during treatment. In another embodiment, the cancer or tumor is a metastasis of an original cancer, i.e., formed by cells that have spread from the original site of the cancer or tumor.

In various embodiments of the methods and compositions described herein, the cancer can include, without limitation, breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, leukemia, myeloma, lymphoma, glioma, and multidrug resistant cancer. In another embodiment, the neoplastic disease is Kaposi's sarcoma, Merkel cell carcinoma, hepatocellular carcinoma (liver cancer), cervical cancer, anal cancer, penile cancer, vulvar cancer, vaginal cancer, neck cancer, head cancer, multicentric Castleman's disease, primary effusion lymphoma, tropical spastic paraparesis, adult T-cell leukemia, Burkitt's lymphoma, Hodgkin's lymphoma, post-transplantation lymphoproliferative disease, nasopharyngeal carcinoma, pleural mesothelioma (cancer of the lining of the lung), osteosarcoma (a bone cancer), ependymoma and choroid plexus tumors of the brain, and non-Hodgkin's lymphoma. In still other embodiments, the cancer may be a systemic cancer, such as leukemia. In one aspect, the cancer is a human glioblastoma. In another aspect, the cancer is a prostate adenocarcinoma. In still another embodiment, the cancer is a lung adenocarcinoma. In one embodiment, the cancer is non-small cell lung adenocarcinoma (NSCLC). In another embodiment, the cancer is squamous cell carcinoma. In another embodiment, the cancer is liver cancer. In another example, the cancer is a multidrug resistant cancer. In one embodiment, the cancer is a drug resistant cancer.

In one embodiment, the cancer is melanoma. In another embodiment, the cancer is a metastatic or refractory melanoma. In another embodiment, the cancer is a breast cancer. In another embodiment, the cancer is a metastatic or refractory breast cancer, e.g., adenocarcinoma.

In one embodiment as exemplified by the data in the examples and figures, the methods of inhibiting growth or spread of a cancer are practiced when the subject has an established malignancy, or a refractory cancer, or a metastatic cancer. Similarly such methods are useful when the subject is newly diagnosed and prior to treatment.

The term "reduce", "inhibit" or "suppress" or variations thereof as used herein refers to the ability of the components (a) and/or (b) or composition described herein to inhibit, retard, suppress, or reduce the growth, proliferation, spread, mestastasis, or refractory behavior of the cancer cells or tumor in the subject.

The term "treating" or "treatment" is meant to encompass administering to a subject one or more compounds or compositions described herein for the purposes of amelioration of one or more symptoms of a cancer. In the case, of a cancer or tumor, a treatment includes inhibiting the growth, proliferation, size and/or spread of the cancer or tumor.

By "administering" or "route of administration" is delivery of the small molecule kinase inhibitor of a target enzyme of the MEK/MAPK pathway and/or the molecule that induces T cell proliferation, with or without a pharmaceutical carrier or excipient, or with or without another chemotherapeutic agent into the subject systemically or into the environment of the cancer cell or tumor microenvironment of the subject. Conventional and pharmaceutically acceptable routes of administration include, but are not limited to, systemic routes, such as intraperitoneal, intravenous, intranasal, intravenous, intramuscular, intratracheal, subcutaneous, and other parenteral routes of administration or intratumoral or intranodal administration. In one embodiment, the route of administration is oral. In another embodiment, the route of administration is intraperitoneal. In another embodiment, the route of administration is intravascular. Routes of administration may be combined, if desired. In some embodiments, the administration is repeated periodically.

By "chemotherapeutic agent or therapy" is meant a drug or therapy designed for using in treating cancers. One of skill in the art would readily be able to select a chemotherapeutic for formulations with or for administration with the small molecule inhibitor of a target enzyme of the MEK/MAPK pathway and/or the molecule that induces T cell proliferation based on consideration of such factors as the cancer being treated and stage of the cancer, the subject's age and physical condition, among others factors. Examples of chemotherapeutics which may be utilized as described herein include, without limitation, cisplatin, carboplatin, 5-fluorouracil, cyclophosphamide, oncovin, vincristine, prednisone, rituximab, mechlorethamine, cyclophosphamide, ifosfamide, melphalan, chlorambucil, carmustine, lomustine, semustine, thriethylenemelamine, triethylene thiophosphoramide, hexamethylmelamine altretamine, busulfan, triazines dacarbazine, methotrexate, trimetrexate, fluorodeoxyuridine, gemcitabine, cytosine arabinoside, 5-azacytidine, 2,2'-difluorodeoxycytidine, 6-mercaptopurine, 6-thioguanine, azathioprine, 2'-deoxycoformycin, erythrohydroxynonyladenine, fludarabine phosphate, 2-chlorodeoxyadenosine, camptothecin, topotecan, irinotecan, paclitaxel, vinblastine, vincristine, vinorelbine, docetaxel, estramustine, estramustine phosphate, etoposide, teniposide, mitoxantrone, mitotane, or aminoglutethimide. Other therapies for use with the methods and compositions using the small molecule inhibitor of a target signaling molecule/enzyme of the MEK/MAPK pathway and/or the molecule that induces T cell proliferation as described herein include non-chemical therapies. In one embodiment, the additional or adjunctive therapy includes, without limitation, radiation, acupuncture, surgery, chiropractic care, passive or active immunotherapy, X-ray therapy, ultrasound, diagnostic measurements, e.g., blood testing. In one embodiment, these therapies are be utilized to treat the patient. In another embodiment, these therapies are utilized to determine or monitor the progress of the disease, the course or status of the disease, relapse or any need for booster administrations of the compounds discussed herein.

The term "MEK/MAPK pathway" or "MAPK signaling pathway" refers to a chain of proteins in the cell that communicates a signal from a receptor on the surface of the cell to the DNA in the nucleus of the cell and play a key role in the regulation of gene expression, cellular growth, and survival. MAPK signaling is initiated by receptor tyrosine kinases upon their activation by growth factors in the extracellular space. Adaptor molecules that interact directly with the intracellular portion of the receptor mediate the recruitment and activation of signaling molecules of this pathway.

The phrase "target signaling molecule/enzyme of the MEK/MAPK pathway" includes Ras, Raf, MEK, and ERK, the latter also known as MAPK. MEK 1 and 2 are dual specificity threonine/tyrosine kinases often upregulated in various cancer cell types and play a key role in the activation of the signaling pathway that regulates cell growth.

The term "inhibitor or antagonist" of a target signaling molecule or enzyme of the MEK/MAPK pathway includes small chemical/pharmaceutical molecules, peptides, nucleotide sequences, e.g., siRNA or shRNAs, and intracellular antibodies that have the ability to penetrate the cell and bind or interact with the targeted MEK/MAPK pathway gene or its expression product so as to prevent or inhibit or oppose the normal expression or activity of the targeted member of the pathway or to interrupt, prevent or inhibit or oppose the normal activity of the pathway itself. This inhibition suppresses or retards for a certain time period the biological activity that is normally facilitated by the targeted kinase or the entire pathway. In one embodiment, the inhibitor targets multiple signaling molecules of the MEK/MAPK pathway. In another embodiment, the inhibitor targets a single signaling molecule/enzyme of that pathway.

Various inhibitors of the chain of proteins of the MEK/MAPK pathway are identified below in Table 1, as are their targets, e.g., Ras, Raf, MEK, and ERK. Many additional inhibitors are known in the art. For example, trametinib, also known as GSK1120212, is a small molecule with the chemical formula $C_{26}H_{23}FIN_5O_4$. It is an orally bioavailable inhibitor of mitogen-activated protein kinase (MEK MAPK/ERK kinase). Trametinib specifically binds to and inhibits MEK 1 and 2, resulting in an inhibition of growth factor-mediated cell signaling and cellular proliferation in various cancers. Trametinib is a MEK inhibitor in clinical trials. Other MEK inhibitors include AZD6244 (selumetinib; $C_{17}H_{15}BrClFN_4O_3$ as described in MCE MedChem Express; and in Huynh H et al, Mole Cancer Ther. 2007, 6 (1):138-146 among other publications), GDC0973 ($C_{21}H_{21}F_3IN_3O_2$ as described in MCE MedChem Express; and Hoeflich K P, et al. Cancer Res. 2012 Jan. 1; 72(1):210-9), GDC0623 ($C_{16}H_{14}FIN_4O_3$ as described in MCE MedChem Express; and Hatzivassiliou G, et al. 2013 Nature. 501(7466):232-6), refametinib (as described in Canadian Patent Appln CA2923990), Binimetinib (Array BioPharma), MK1833 (balamapimod; PubChem ID No. 11478684, $C_{30}H_{32}ClN_7OS$) and U0126 ($C_{18}H_{16}N_6S_2$; PubChem ID Nol. 3006531). In another embodiment, where the target is ERK, an ERK inhibitor is SCH772984 ($C_{33}H_{33}N_9S_2$; PubChem ID Nol. 24866313). As used throughout this specification, trametinib is the prototype of an inhibitor or antagonist of the prototype target, MEK, of the MEK/MAPK pathway for use in the methods and compositions described herein. It should be understood that one of skill in the art given the teachings of this specification may readily select another signaling molecule of MEK/MAPK and an appropriate inhibitor of that target.

Other small molecule inhibitors or antagonists of target signaling molecules/enzymes in the MEK/MAPK pathway include those known in the art to antagonize the indicated pathway targets and their salts derived from pharmaceutically or physiologically acceptable acids, bases, alkali metals and alkaline earth metals. Still other inhibitors useful in the methods described herein may be found in the catalogs of various biochemical and pharmaceutical suppliers. Physiologically acceptable acids include those derived from inorganic and organic acids. A number of inorganic acids are known in the art and include, without limitation, hydrochloric, hydrobromic, hydroiodic, sulfuric, nitric, and phosphoric acid. A number of organic acids are also known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids. Inhibitor compound salts can be also in the form of esters, carbamates, sulfates, ethers, oximes, carbonates, and other conventional "pro-drug" forms, which, when administered in such form, convert to the active moiety in vivo. In one embodiment, the prodrugs are esters. The inhibitor compounds discussed herein also encompass "metabolites" which are unique products formed by processing the selected inhibitor compound by the cell or subject. In one embodiment, metabolites are formed in vivo.

Also useful in suppressing or down-regulating the expression, activity or phosphorylation of the target of the inhibitors are "antisense" nucleotide sequence or a small nucleic acid molecule having a complementarity to a target nucleic acid sequence, e.g., Ras, MEK, etc. It can also comprise a nucleic acid sequence having complementarity to a sense region of the small nucleic acid molecule. For example, in one embodiment the composition comprises a nucleic acid construct comprising a sequence that reduces or suppresses the expression of one of the targets or a combination thereof in the target cancer cells. For example, the inhibiting composition can include a nucleic acid construct comprising a short nucleic acid molecule selected from the group consisting of a short hairpin RNA (shRNA), a short interfering RNA (siRNA), a double stranded RNA (dsRNA), a micro RNA, and an interfering DNA (DNAi) molecule, optionally under the control of a suitable regulatory sequence.

"A molecule that induces T cell proliferation" or "proliferative cytokine" as used herein is meant a molecule or proliferative cytokine or an agonist of a proliferative cytokine that can stimulate proliferation, differentiation, and cell migration of T cells. In one embodiment the T cells are CD4 T cells. In another embodiment the T cells are CD8 T cells. In one embodiment, this stimulation occurs in the presence of the pathway inhibitors described above. In one embodiment, this stimulation occurs both in the absence and presence of the pathway inhibitors described above. The function of the cytokines or cytokine agonist can depend on the target cell, environment of the target cell, culture conditions, cofactors or synergistic effects. Representative proliferative cytokines for use in the methods and compositions herein include IL-15, IL-2, or IL-7 used independently. In another embodiment, the useful cytokines are a combination of IL-15 and IL-2 or a combination of IL-15 and IL-7. In another embodiment, the useful cytokines are a combination of IL-2 and IL-7. In still a further embodiment, the useful cytokines are a combination of IL-15, IL-2 and IL-7.

"IL-15" is one of the proliferative cytokines, and is an essential survival factor for natural killer (NK), natural killer-like T (NKT), and CD44hi memory CD8 T cells. The bioactivity of IL-15 in vivo is conferred mainly through a trans-presentation mechanism in which IL-15 is presented in complex with the α-subunit of soluble IL-15 receptor (IL-15R) to NK, NKT or T cells rather than directly interacts with membrane-bound IL-15R.[43]

"Agonist of a proliferative cytokine" refers to a molecule capable of stimulating or mimicking the biological activity in vivo and/or binding with the cytokine receptor on a cell. In one embodiment, the agonist is an IL-15 agonist. Among available IL-15 agonists are those which consist of IL-15 and partial or whole sequence of soluble IL-15R. In one embodiment, an IL-15 agonist is a molecule generated from a pre-association of IL-15 and its soluble receptor a-subunit-Fc fusion to form IL-15:IL-15Rα-Fc complex. In another embodiment, an IL-15 agonist is a molecule generated by the expression of the hyperagonist IL-15-sIL-15Rα-sushi fusion protein consisting of IL-15 and the recombinant soluble sushi domain of IL-15Rα which was identified to have the most binding affinity for IL-15. In still another embodiment, the triple fusion protein combining Apolipoprotein A-I, IL-15 and 15Rα-sushi is similarly useful (see, on-line publication by DIGNA Biotech). In yet another embodiment, an IL-15 agonist is a fusion protein of human IL-15 mutant IL-15N72D (residue substitution at position 72) with the soluble domain of IL-15Rα. ALT-803 is a fusion protein of IL-15N72D and IL-15RαSu/Fc as a stable soluble complex (Altor Bioscience). As used throughout this specification, ALT-803 is the prototype of a proliferative cytokine agonist for use in the methods and compositions described herein. Still other IL-15 agonists include heterologous forms of IL-15 and its fragments (see, e.g., US Patent Application Publication No. US2015/0359853). Suitable IL-15 agonists such as the above are described in below-listed References 43 (Wu) and 45 (Zhu) and the documents cited therein, all incorporated herein by reference.

In other embodiments, the agonist is an IL-2 agonist. In another embodiment, the agonist is an IL-7 agonist. Agonists of the proliferative cytokines for use in the methods and compositions herein include agonists of IL-15, IL-2, or IL-7 used independently. In another embodiment, the useful agonists are a combination of IL-15 agonist and IL-2 agonist or a combination of IL-15 agonist and IL-7 agonist. In another embodiment, the useful cytokine agonists are a combination of IL-2 agonist and IL-7 agonist. In still a further embodiment, the useful cytokine agonists are a combination of IL-15 agonist, IL-2 agonist and IL-7 agonist.

By "pharmaceutically acceptable carrier or excipient" is meant a solid and/or liquid carrier, in dry or liquid form and pharmaceutically acceptable. The compositions are typically sterile solutions or suspensions. Examples of excipients which may be combined with the small molecule inhibitor of the MEK/MAPK pathway and/or the molecule that induces T cell proliferation include, without limitation, solid carriers, liquid carriers, adjuvants, amino acids (glycine, glutamine, asparagine, arginine, lysine), antioxidants (ascorbic acid, sodium sulfite or sodium hydrogen-sulfite), binders (gum tragacanth, acacia, starch, gelatin, polyglycolic acid, polylactic acid, poly-d,l-lactide/glycolide, polyoxaethylene, polyoxapropylene, polyacrylamides, polymaleic acid, polymaleic esters, polymaleic amides, polyacrylic acid, polyacrylic esters, polyvinylalcohols, polyvinylesters, polyvinylethers, polyvinylimidazole, polyvinylpyrrolidon, or chitosan), buffers (borate, bicarbonate, Tris-HCl, citrates, phosphates or other organic acids), bulking agents (mannitol or glycine), carbohydrates (such as glucose, mannose, or dextrins), clarifiers, coatings (gelatin, wax, shellac, sugar or other biological degradable polymers), coloring agents, complexing agents (caffeine, polyvinylpyrrolidone, β-cyclodextrin or hydroxypropyl-β-cyclodextrin), compression aids, diluents, disintegrants, dyes, emulsifiers, emollients, encapsulating materials, fillers, flavoring agents (peppermint or oil of wintergreen or fruit flavor), glidants, granulating agents, lubricants, metal chelators (ethylenediamine tetraacetic acid (EDTA)), osmo-regulators, pH adjustors, preservatives (benzalkonium chloride, benzoic acid, salicylic acid, thimerosal, phenethyl alcohol, methylparaben, propylparaben, chlorhexidine, sorbic acid, hydrogen peroxide, chlorobutanol, phenol or thimerosal), solubilizers, sorbents, stabilizers, sterilizer, suspending agent, sweeteners (mannitol, sorbitol, sucrose, glucose, mannose, dextrins, lactose or aspartame), surfactants, syrup, thickening agents, tonicity enhancing agents (sodium or potassium chloride) or viscosity regulators. See, the excipients in "Handbook of Pharmaceutical Excipients", 5$^{th}$ Edition, Eds.: Rowe, Sheskey, and Owen, APhA Publications (Washington, D.C.), 2005 and U.S. Pat. No. 7,078,053, which are incorporated herein by reference. The selection of the particular excipient is dependent on the nature of the compound selected and the particular form of administration desired.

Solid carriers include, without limitation, starch, lactose, dicalcium phosphate, microcrystalline cellulose, sucrose and kaolin, calcium carbonate, sodium carbonate, bicarbonate, lactose, calcium phosphate, gelatin, magnesium stearate, stearic acid, or talc. Fluid carriers without limitation, water, e.g., sterile water, Ringer's solution, isotonic sodium chloride solution, neutral buffered saline, saline mixed with serum albumin, organic solvents (such as ethanol, glycerol, propylene glycol, liquid polyethylene glycol, dimethylsulfoxide (DMSO)), oils (vegetable oils such as fractionated coconut oil, arachis oil, corn oil, peanut oil, and sesame oil; oily esters such as ethyl oleate and isopropyl myristate; and any bland fixed oil including synthetic mono- or diglycerides), fats, fatty acids (include, without limitation, oleic acid find use in the preparation of injectables), cellulose derivatives such as sodium carboxymethyl cellulose, and/or surfactants.

By "effective amount of the small molecule inhibitor of the MEK/MAPK pathway" is meant the amount or concentration (by single dose or in a dosage regimen delivered per day) sufficient to retard, suppress or kill cancer or tumor, while providing the least negative side effects to the treated subject. In one embodiment, the effective amount of the inhibitor is within the range of 0.01 mg/kg body weight to 10 mg/kg body weight in humans including all integers or fractional amounts within the range. In certain embodiments, the effective amount is at least 0.01, 0.03, 0.05, 0.07, 0.09, 0.1, 0.25, 0.5, 0.6, 0.7, 0.8, 0.9, 1, 2, 3, 4, 5, 6, 7, 8, 9, 10 or more mg/kg body weight, including all integers or fractional amounts within the range. In another embodiment, the effective amount is about 0.3 mg/kg (or 2 mg/day/adult patient). In one embodiment, the effective total daily dose per adult is at least 0.1, 0.2, 0.3, 0.4, 0.5, 0.6, 0.7, 0.8, 0.9, 1, 2, 3, 4, 5, 6, 7, 8, 9, or at least 10 or more mg per adult. In another embodiment, these amounts represent a single dose. In another embodiment, the above amounts define an amount delivered to the subject per day. In another embodiment, the above amounts define an amount delivered to the subject per day in multiple doses. In still other embodiments, these amounts represent the amount delivered to the subject over more than a single day.

In one embodiment of the method and compositions described herein, when the inhibitor and cytokine agonist are administered together or sequentially, the effective amount of the small molecule inhibitor is an amount larger than that required when the inhibitor is administered to retard cancer cell growth and spread in a subject in the absence of the cytokine agonist. In another embodiment of the method and compositions described herein, the effective amount of the small molecule inhibitor is an amount lesser than that required when the inhibitor is administered to retard cancer cell growth and spread in a subject in the absence of the cytokine agonist. In another embodiment of the method and compositions described herein, the effective amount of the small molecule inhibitor is less than that required to retard cancer cell growth in a subject in the absence of the cytokine agonist.

By "effective amount of the molecule that induces T cell proliferation" is meant the amount or concentration (by single dose or in a dosage regimen delivered per day) sufficient to stimulate and enhance T cell proliferation in the presence of the small molecule inhibitor of the target member of the MEK/MAPK pathway. In one embodiment, the effective amount of the proliferative cytokine or cytokine agonist is within the range of at least 0.1 µg/kg body weight to 70 µg/kg body weight in humans including all integers or fractional amounts within the range. In one embodiment, the effective amount of IL-15 or IL-15 agonist is at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70 or more µg/kg body weight including all integers or fractional amounts within the range. In one embodiment, the effective total daily dose per adult is at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70 or more µg daily including all integers or fractional amounts within the range. In one embodiment, the above amounts represent a single dose. In another embodiment, the above amounts define an amount delivered to the subject per day. In another embodiment, the above amounts define an amount delivered to the subject per day in multiple doses. In still other embodiments, these amounts represent the amount delivered to the subject over more than a single day.

Effective amounts of IL-2 in certain embodiments can be administered at the same dosages as discussed above for IL-15. Such doses include at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70 or more µg/kg body weight including all integers or fractional amounts within the range. In one embodiment, the effective total daily dose per adult is at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70 or more µg daily including all integers or fractional amounts within the range. In one embodiment, the above amounts represent a single dose. In another embodiment, the above amounts define an amount delivered to the subject per day. In another embodiment, the above amounts define an amount delivered to the subject per day in multiple doses. In still other embodiments, these amounts represent the amount delivered to the subject over more than 2 days. In another embodiment, much higher dosages than those identified above for IL-15 cytokine or its agonist are suitable for administration of IL-2. For example, known dosages of IL-2 include two 5 day cycles (600,000 IU/kg/dose) administered IV over 15 minutes q8h separated by a minimum of 9 days. Still other known administration dosages of IL-2 as known by the pharmaceutical literature are anticipated to be equally useful in the methods and compositions described herein.

In a similar manner, dosages for administration of IL-7 or IL-7 agonists may be the same as those for IL-15 described. Such doses include at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70 or more µg/kg body weight including all integers or fractional amounts within the range. In one embodiment, the effective total daily dose per adult is at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70 or more µg daily including all integers or fractional amounts within the range. In one embodiment, the above amounts represent a single dose. In another embodiment, the above amounts define an amount delivered to the subject per day. In another embodiment, the above amounts define an amount delivered to the subject per day in multiple doses. In still other embodiments, these amounts represent the amount delivered to the subject over more than a week. In yet another embodiment, effective amounts of IL-7 may be similar to the high doses as described above for IL-2. One of skill in the art may readily select a suitable effective amount of IL-7 or an agonist thereof by resort to known pharmaceutical literature.

In one embodiment of the method and compositions described herein, when the pathway inhibitor and the proliferative cytokine or cytokine agonist (hereafter "cytokine/agonist") are administered together or sequentially, the effective amount of the cytokine/agonist is an amount larger than that required when the cytokine/agonist is administered to stimulate T cell production in a subject in the absence of the inhibitor. In another embodiment of the method and compositions described herein, the effective amount of the cytokine/agonist is the same as that required to stimulate T cell production in a subject in the absence of the inhibitor. In another embodiment of the method and compositions described herein, the effective amount of the cytokine/agonist is less than that required to stimulate T cell production in a subject in the absence of the inhibitor. In still further embodiments, the combination of the inhibitor and cytokine/agonist with yet another pharmacological agent or treatment protocol permits lower than usual amounts of the inhibitor and/or cytokine/agonist and additional chemotherapeutic agent to achieve the desired therapeutic effects. In another embodiment, the combination of the pathway inhibitor and cytokine agonist with another chemotherapy treatment protocol permits adjustment of the additional protocol regimen to achieve the desired therapeutic effect.

Methods

In one embodiment, a method of treating a mammalian subject with cancer comprises, in one aspect, administering to the subject having a cancer, a combination therapy. The combination therapy involves administering (a) a small molecule inhibitor of the MEK/MAPK pathway and (b) a molecule that induces T cell proliferation in the presence of the inhibitor. In a specific embodiment, the small molecule inhibitor, i.e., component (a) is trametinib and the inducing molecule is the proliferative IL-15 agonist, i.e., component (b) is ALT-803. Other selections of components (a) and (b) may be selected from those mentioned or incorporated by reference into this application or those indicated in the examples and Table 1. The combination of components (a) and (b) reduce the proliferation of the cancer and tumor cells in vivo.

In another embodiment, a method of treating a mammalian subject with cancer comprises, in one aspect, administering to the subject having a metastatic or refractory cancer or tumor, a combination therapy. The combination therapy involves administering a small molecule inhibitor of the MEK/MAPK pathway and a molecule that induces T cell proliferation in the presence of the inhibitor.

In one embodiment of the method, the administration of (a) occurs before the administration of (b). In another embodiment of the method, the administration of (a) occurs after the administration of (b). In still another embodiment of the method, the administration of (a) occurs substantially simultaneously with the administration of (b). In the examples below, a component (a), trametinib, was administered once daily from days 3-13 and a component (b), ALT-803, administered on days 3, 8, and 13.

The method of delivering the pathway inhibitor in concert or sequentially with the proliferative cytokine/agonist further includes administering repeated doses of one or more of component (a) or component (b) to the subject. As illustrated in the examples below, this method of treatment prevents recurrence of aggressive tumors through the generation of protective immunity.

The methods of treatment of cancer described herein further includes administering components (a) and (b) with any other therapeutic agent via any conventional route, including the routes described in detail above.

Pharmaceutical Compositions or Formulations

In another aspect, compositions or kits containing components (a) and (b) are further described herein for use in the treatment of cancer, including a metastatic or refractory cancer or tumor. In one embodiment a pharmaceutical composition contains a combination of (a) an effective amount of a small molecule inhibitor of a target member of the MEK/MAPK pathway to reduce, inhibit or suppress growth of the cancer or tumor; and (b) an effective amount of a molecule that induces T cell proliferation in the presence of said inhibitor. This induction is in the microenvironment of the tumor or in occurs systemically in vivo. The components (a) and (b) in one embodiment are admixed. In another embodiment, they are separately available, e.g., as in separate ampoules.

In certain embodiments, the components (a) and (b) are individually or together formulated with a pharmaceutically acceptable carrier or diluent. In one aspect, the pharmaceutical composition contains, e.g., about 25, 30, 35, 40, 45, 50, 55, 60, 65, 70, 75, 80, 85, to about 90% of the inhibitor and/or cytokine/agonist in combination with a pharmaceutical carrier or excipient. The pharmaceutical excipients may be one of more of those identified above. The composition or kit may also contain components (a) and (b) in lyophilized form and provide the diluents in the kit.

In one example, the composition comprises the inhibitor, trametinib, admixed or separately associated with a proliferative cytokine or an agonist of a proliferative cytokine, such as a cytokine/agonist specified above. In one embodiment, the cytokine is IL-15 and the cytokine agonist is an IL-15 agonist, such as ALT-803. In another embodiment, the cytokine is IL-2.

The compositions and/or a kit may provide the components (a) and (b), with or without an additional chemotherapeutic. The compositions and/or kits may provide suitable pharmaceutically acceptable diluents, carriers or other pharmaceutical ingredients for admixture with component (a) or component (b) before administration.

Specific Embodiments

The following examples elucidate the effects of multiple targeted therapies on the tumor immunoenvironment and, subsequently, anti-tumor immunity. The inventors analyzed a panel of molecules for activity on human T cells and then focused on dissecting the role of an exemplary kinase inhibitor, trametinib, in restricting the growth of a KRas-driven tumor cell line in immune-competent mice. The results indicate that, in vivo, trametinib exerts divergent effects on at least 3 different cells types, resulting in significant differences in the accumulation of suppressive myeloid cells at tumor beds and therefore, despite a direct suppressive effect on T cells, a boost in anti-tumor immunity.

A potential mechanism to reconcile these divergent results is that trametinib acts on multiple tumor and non-tumor cells in the tumor microenvironment that, overall, make its effects very different in vitro and in vivo. One of these effects involves alterations in the secretion of cytokines by intrinsically inflammatory, tumor cells. Among these, osteopontin has been implicated in the recruitment of macrophages into tumors[10] and its expression is positively correlated with CD204+ M2-like macrophages[11]. Osteopontin secreted by tumor cells also drives the expansion of MDSCs in the spleens of tumor bearing mice through activation of the ERK1/2-MAPK pathway in myeloid progenitors[12].

Additionally, to examine the ability of an exemplary agonist of a proliferative cytokine, IL-15, ALT-803 (Altor Pharmaceuticals) to rescue the immunosuppressive effect of MEK and pan-PI3K inhibitors on the anti-tumor immune response, the inventors conducted in vitro experiments to verify that ALT-803 can restore the proliferation of activated human T cells, similar to or greater than that of IL-15, in the presence of the MEK inhibitor GSK-1120212 (trametenib) or the pan-PI3K inhibitor BKM-120. By analyzing the proliferation of OT-I T cells adoptively transferred into mice bearing ovalbumin-expressing tumors during the administration of trametinib, BKM-120, ALT-803, trametinib plus ALT-803, or BKM-120 plus ALT-803, the inventors determined that ALT-803 has a beneficial effect on the anti-tumor immune response when used in combination with the IL-15 agonist ALT-803.

ELISPOT analysis measured IFN-gamma and GranzymeB responses of tumor specific T cells. Disease progression in tumor bearing mice treated with trametinib, BKM-120, AL T-803, trametinib plus ALT-803, or BKM-120 plus ALT-803, was examined and demonstrated that ALT-803 synergizes with the MEK inhibitor to provide enhanced therapeutic effect.

The following examples are provided for the purpose of illustration. These examples should be construed to encompass any and all variations that become evident as a result of the teaching provided herein.

EXAMPLE 1: Methods and Materials

Mice—WT C57BL/6 and congenic Ly5.1 female 6-8 week old mice were procured from the National Cancer Institute or Charles River Laboratory. OT1 C57BL/6-Tg (TcraTcrb)1100 Mjb/J transgenic mice were obtained from Jackson Labs. Transgenic KRastm4Tyj and Trp53tm1Brn mice[28,29] were obtained from NCI Mouse Models of Human Cancers Consortium, brought to a full C57BL/6 background[17,38]. All mice were randomized into treatment groups.

Cell lines and media—The Brpkp110 primary mammary tumor cell line was generated by culturing a mechanically dissociated B6 L-Stop-L-KRas$^{G12D}$p53$^{flx/flx}$L-Stop-L-Myristoylated p110α-GFP/+primary breast tumor mass[27]. Tumor cells were passaged a total of 10 times before deriving the Brpkp110 cell line.

A2780 cells were obtained from AddexBio Technologies. ID8 cells[39] were provided by K. Roby (Department of Anatomy and Cell Biology, University of Kansas, Kansas City, Kans.) and retrovirally transduced to express Defb29 and Vegf-a[40] or OVA[25]. Lewis Lung Carcinoma cells (LLC) were obtained from ATCC. A2780 cells were cultured in D10 (DMEM (CellGro, with HEPES, glucose, and L-glutamine, without sodium pyruvate), 10% FBS, penicillin (100 I.U./ml), streptomycin (100 μg/ml), L-glutamine (2 mM), sodium pyruvate (0.5 mM), β-mercaptoethanol (50 μM)). All other cell lines and lymphocytes were cultured in R10 (RPMI-1640 (CellGro, with L-glutamine), 10% FBS, penicillin (100 I.U./ml), streptomycin (100 μg/ml), 1-glutamine (2 mM), sodium pyruvate (0.5 mM), β-mercaptoethanol (50 μM)).

Compounds and cytokines—ALT-803 was generously provided by Altor BioScience and was diluted in sterile PBS for in vitro and in vivo assays. Recombinant human IL-15 (Novoprotein), recombinant human IL-2 (Peprotech), recombinant mouse IL-7 (Peprotech), and Concanavalin A (Type VI, Sigma-Aldrich) were reconstituted in sterile PBS and stored at −20° C. Trametinib (GSK-1120212) was purchased from LC Laboratories and suspended in vehicle solution of 10% PEG-300 (Sigma Aldrich) and 10% Cremophor EL (EMD Millipore) in sterile dH$_2$O for in vivo oral gavage experiments. For in vitro assays, all inhibitors (including trametinib) were dissolved in sterile DMSO and diluted in the assays 1:1000, so that the final concentration of DMSO was 0.1%. For CD8 depletion, mice were injected with anti-CD8α (BioXcell, clone YTS 169.4) on day 3 (500 μg/mouse) and day 10 (250 μg/mouse) post tumor inoculation. All antibodies, including isotype control (BioXcell, clone LTF-2), were injected i.p. in sterile PBS.

Tumor inoculation—Brpkp110 tumors were initiated by injecting 5×10$^5$ cells subcutaneously into the axillary region. LLC tumors were initiated by injection of 2×10$^5$ cells either intraperitoneally or into the axillary region subcutaneously. Tumor volume was calculated as: 0.5×(L×W$^2$), where L is length, and W is width.

T cell stimulation—For human T cell proliferation assays, peripheral blood lymphocytes were obtained by leukopheresis/elutriation and Miltenyi bead-purified and K562 cells expressing human CD32 were generated as previously described[41]. K32 were γ-irradiated (100 Gy) and loaded with anti-CD3 (500 ng/ml, clone OKT3; eBioscience) plus anti-CD28 (500 ng/ml, clone 15E8; EMD Millipore) antibodies at room temperature for 10 minutes. PBMCs were labeled with CELLTRACE Violet stain (Invitrogen) according to the manufacturer's instructions and cocultured with loaded K32 cells at a 10:1 T cells:K32 ratio or activated with ConA (2 μg/ml, Sigma). Proliferation of stimulated T cells was determined 7 days later by FACS and Division Index was calculated using FlowJo software.

For mouse T cell proliferation assays, pan-T cells were negatively purified with antibodies to B220 (RA3), Mac-1 (M170.13), and MHC-II (M5/114) using magnetic beads. T cells were labeled with CELLTRACE Violet (Invitrogen) and stimulated with either agonistic CD3/CD28 beads (Dynabeads, Life Technologies) or tumor-pulsed bone marrow dendritic cells (BMDCs) and analyzed for proliferation by FACS either 3 days (CD3/CD28 beads) or 7 days (BMDCs) later. Day 7 BMDCs were generated as previously described[44] and cultured overnight with double-irradiated (γ-irradiated, 100 Gy; and UV, 30 min) ID8-Defb29/Vegf-A cells. BMDCs were added to cultures of T cells at a 10:1 (T cell:BMDC) ratio. For recall ELISpot assays, mouse T cells were primed with tumor-pulsed BMDCs plus IL-2 (30 U/ml) and IL-7 (5 ng/ml), and restimulated 7 days later with fresh tumor-pulsed BMDCs at a 10:1 ratio in an IFN-γ ELISpot (eBioscience).

Cell proliferation assays—Cells were plated in 96-well plates. Compounds were added the next morning, and cell proliferation was measured 48 hrs later with the CELLTI-TER 96 MTS assay (Promega) according to the manufacturer's instructions. Molecular screening of compounds on A2780 cells was performed by adding compounds the morning after plating in 384-well plates and measuring proliferation 72 hrs later with resazurin fluorescence. Normalized percent inhibition (NPI) was calculated with respect to fluorescence values obtained with DMSO negative control and doxorubicin (5 μM) positive control as NPI=100%* (DMSO−compound)/(DMSO−doxorubicin). TCR ligation of human CD8 T cells CD8+ cells were sorted from PBMCs and rested overnight in R10. T cells (0.5×10$^6$ per condition) were stained with OKT3-biotin (BioLegend, 10 μg/ml) for 15 mins on ice, and washed in cold PBS. TCR ligation was performed by adding streptavidin (Promega, 25 μg/ml) and anti-CD28 (Millipore, clone 15E8, 1 μg/ml) in the presence of indicated inhibitors for 10 min at 37° C.

In vivo OT-I proliferation—Congenic Ly5.1 mice were injected with 1.5×10$^6$ ID8-OVA cells i.p[25]. On day 10, mice were injected i.p. with 1.5×10$^6$ CELLTRACE Violet-labeled, naïve OT-I T cells, and administered ALT-803 (0.2 mg/kg) or PBS i.p. Mice were gavaged with trametinib or vehicle on days 9-13. On day 14, mice were euthanized and peritoneal washes were analyzed for proliferating OT-I T cells.

In vitro MDSC differentiation, suppression, and chemotaxis—Bone marrow from naïve mice was cultured for 4 days with IL-6 (40 ng/ml, Peprotech) and GM-CSF (40 ng/ml Peprotech) or media containing 50% tumor-conditioned media, prepared by filtering supernatant from a confluent flask of tumor cells through a 0.45 μm membrane. For suppression assays, MDSCs were added to 2×10$^5$ CellTrace-labelled, WT splenocytes simultaneously activated with anti-CD3 (500 ng/ml, clone 2C11, Tonbo) and anti-CD28 (1 μg/ml, clone 37.51, Tonbo) in 96 well plates. Proliferation of T cells was measured 3 days later. For chemotaxis assays, MDSCs were separated into Ly6G+ and Ly6G− fractions with anti-Ly6G MicroBeads (Miltenyi) according to the manufacturer's protocol. Chemotaxis was measured toward recombinant carrier-free osteopontin (R&D Systems) after 1 hr on 3 μm filter plates (Ly6G+ cells) or 4 hrs on 5 μm filter plates (Ly6G− cells) (NeuroProbe).

Western blotting—Cells were lysed in RIPA buffer (Thermo Scientific) with protease inhibitors (Complete Protease Inhibitor Cocktail Tablets, Roche) and phosphatase inhibitors (Halt Phosphatase Inhibitor, Thermo Scientific, and $Na_3VO_4$, 1 mM) and cleared by centrifugation. Proteins were quantified by BCA assay (Thermo Scientific), diluted in reducing lamelli buffer, denatured by incubation at 95° C., run on mini Protean TGX Ready Gels (Bio-Rad Laboratories), transferred to a nitrocellulose membrane, blocked, and incubated with primary antibodies for p-ERK1/2 (Cell Signaling Technologies, clone D13.14.4E), p-AKT (Cell Signaling Technologies, clone D9E), beta-tubulin (Cell Signaling Technologies, clone 9F3), beta-actin (Sigma, clone AC-15), or IGF-1R (Cell Signaling Technologies, #3027). Immunoreactive bands were developed using horseradish peroxidase-conjugated secondary antibodies (Bio-Rad Laboratories) and ECL substrate (GE Healthcare).

Immunohistochemistry—Tissues were embedded in Tissue-Tek OCT and frozen. Endogenous peroxidases were quenched from acetone-fixed sections (8 μm) by incubating in 0.3% $H_2O_2$ for 10 minutes at room temperature. Following quenching, sections were blocked using 3% goat serum followed by staining with antibodies against Ki-67 (clone D3B5, Cell Signaling Technology). Immunohistochemistry using the ABC Kit (Vector labs) was performed according to the manufacturer's instructions, and sections were counter stained with hematoxylin. Slides were then imaged at 10× objective magnifications on a Nikon E600 Upright microscope with a Nikon DS-Ri1 Digital camera. Nikon NIS-Elements software was used for image acquisition and image stitching of the entire tumor. The 'Grab Large Image' function in the NIS-Elements software was used to create each tiled image. Acquisition parameters were standardized for imaging of all samples, exposure, white balance, and bit depth. Additionally, each image was spatially calibrated. Image Pro Plus 7 analysis software was used to measure the percentage of Ki67 stained nuclei within each sample. To calculate the total area of each sample, a perimeter outline Area of Interest (AOI) was created to isolate the sample from background. This process was automated by creating a macro to extract the green channel, apply an open filter, threshold image by intensity. Ki67 nuclei were thresholded by selecting a specific color brown stain. An area restriction filter was set to remove debris. Percentage of stained nuclei was calculated as total area of brown stained nuclei divided by total AOI of sample.

LC-MS/MS—Brpkp110 cells were cultured in serum-free RPMI with DMSO or trametinib for 40 hrs. Supernatants were collected, centrifuged, passed through a 0.22 μm filter, and concentrated by centrifugation in Amicon 3000 MWCO tubes (EMD Millipore). Concentrated sups were run 0.5 cm on a NuPage 12% Gel with MES buffer, extracted, and digested with trypsin.

Liquid chromatography tandem mass spectrometry (LC-MS/MS) analysis was performed by the Wistar Proteomics Facility using a Q Exactive Plus mass spectrometer (Thermo Scientific) coupled with a Nano-ACQUITY UPLC system (Waters). Samples were injected onto a UPLC Symmetry trap column (180 μm i.d.×2 cm packed with 5 μm C18 resin; Waters), and tryptic peptides were separated by RP-HPLC on a BEH C18 nanocapillary analytical column (75 μm i.d.×25 cm, 1.7 μm particle size; Waters) using a gradient formed by solvent A (0.1% formic acid in water) and solvent B (0.1% formic acid in acetonitrile). Peptides were eluted at 200 nL/min for 5-30% B over 225 min, 30-80% B over 5 min, constant 80% B for 10 min before returning to 5% B over 1 min. A 30-min blank gradient was run between sample injections to minimize carryover. Eluted peptides were analyzed by the mass spectrometer set to repetitively scan m/z from 400 to 2000. The full MS scan was collected at 70,000 resolution followed by data-dependent MS/MS scans at 17,500 resolution on the 20 most abundant ions exceeding a minimum threshold of 20,000. Peptide match was set as preferred, exclude isotopes option and charge-state screening were enabled to reject singly and unassigned charged ions.

MS data were analyzed with MaxQuant 1.5.2.8 software[42]. MS/MS data were searched against the mouse UniProt protein database (July 2014) using full trypsin specificity with up to two missed cleavages, static carboxamidomethylation of Cys, and variable oxidation of Met and protein N-terminal acetylation. Consensus identification lists were generated with false discovery rates of 1% at protein and peptide levels. Reverse hits and contaminants were removed from all datasets.

ELISA—Mouse and human osteopontin concentrations were measured using ELISA kits (RayBiotech) according to the manufacturer's instructions. Plasma was isolated from peripheral blood of mice by centrifugation in lithium heparin tubes (Becton Dickinson).

Statistics—Unless indicated otherwise, all data shown represent means with SEM. All hypothesis testing was two-sided, and a significance threshold of 0.05 for P was used. Unpaired t-tests were performed unless indicated otherwise. Analyses were carried out using GraphPad Prism software. Experiments were repeated at least twice unless otherwise indicated.

Study Approval—All animals were maintained in specific pathogen free barrier facilities and used in accordance with the Institutional Animal Care and Use Committee of the Wistar Institute.

EXAMPLE 2: Small Molecule Inhibitors Suppress Human T Cell Activation In Vitro

To determine the sensitivity of human T cells to inhibition of signaling pathways commonly targeted in cancer therapy, we first designed a high-throughput assay to test a diverse panel of 41 inhibitors over a 6 log concentration range on Concanavalin A (ConA)-induced activation and expansion of human T cells. At doses equivalent to or below those required to limit proliferation of A2780 ovarian cancer cells known to be sensitive to PI3K and MEK inhibitors[13, 14]—a variety of inhibitor classes prevented ConA-driven T cell expansion (FIG. 1A). Those included small molecules targeting PI3K, mTOR, MAPK, and CDK signaling, as well as transcriptional regulators (HDACs) and survival molecules (Bcl-2). Among them, trametinib, the MEK inhibitor approved by the FDA for BRAF-mutant melanoma, was quite potent at inhibiting the in vitro proliferation of human T cells. Overall, the observed EC50 of every molecule with some activity on A2780 cells was lower for human T cells than A2780 cells, as shown in Table 1.

Table 1 lists the small molecule names, targets, and EC50 values on T cells and A2780 cells for each compound. EC50 values were calculated from normalized percent inhibition data using non-linear curve fitting in PRISM software. N/A indicates ambiguous curve fits or EC50 values greater than the highest concentration tested (25 μM).

TABLE 1

| Target | Molecule | EC50 - T cells | EC50 - A2780 ovarian cancer cells |
|---|---|---|---|
| BRAF | GSK436 (dabrafenib) | 1.28 | 11.4 |
| BRAF | PLX4032 (vemurafenib) | 5.26 | N/A |
| ERK | SCH772984 | 0.0222 | 7.64 |
| MEK | AZD6244 (selumetinib) | 24.5 | N/A |
| MEK | GDC0973 | 0.00435 | 9.04 |
| MEK | GSK1120212 (trametinib) | 0.000337 | N/A |
| MEK | U0126 | 1.92 | 12.6 |
| RAF/VEGF | RAF265 | 0.128 | 5.63 |
| AKT | GSK2141795 | 0.0960 | 2.35 |
| AKT | MK2206 | 0.446 | 8.75 |
| mTOR | INK128 | 0.0184 | 0.257 |
| mTOR | OSI027 | 0.311 | 5.88 |
| mTOR | Rapamycin | 0.00403 | N/A |
| PI3K | LY294002 | 2.69 | 17.2 |
| PI3K | PX-866 | 1.20 | N/A |
| PI3K beta | AZD6482 | 0.962 | N/A |
| PI3K pan | BEZ235 | 0.00240 | 0.0210 |
| PI3K pan | BKM120 | 0.239 | 11.5 |
| PI3K pan | GDC0941 | 0.0500 | 1.54 |
| PI3K pan | GSK2126458 | 0.000237 | 0.155 |
| abl/PDGFR/ckit | STI571 (imatinib) | 9.00 | 20.8 |
| Aurora B | MLN8237 | 0.0868 | N/A |
| Aurora A | AZD1152 | 0.0921 | N/A |
| Aurora kinase | SNS314 | 0.0729 | 5.83 |
| autophagy | Spautin-1 | N/A | N/A |
| bcl-2 | ABT737 | 0.0610 | N/A |
| bcl-2 | obatoclax | 0.0567 | 1.11 |
| BcrAbl/Kit/DDR/Eph | AMN107 | 2.48 | 19.1 |
| c-MET | AMG208 | N/A | N/A |
| CDK | SCH727965 | 0.00273 | 2.94 |
| CDK4/6 | LEE011 | 2.93 | N/A |
| CDK4/6 | PD0332991 | 0.110 | 5.21 |
| HDAC | LBH589 | 0.0250 | 3.61 |
| IGF-1R | AG1024 | 9.83 | 21.3 |
| IGF-1R | GSK1904529 | 13.9 | N/A |
| IGF-1R | OSI906 | N/A | N/A |
| p53 | nutlin-3a | 1.13 | 16.8 |
| porcupine | LGK974 | 9.03 | 24.4 |
| smoothened | LDE225 | 3.57 | 8.48 |
| Src | AZD0530 (saracatinib) | 0.422 | N/A |

Figure 1B:
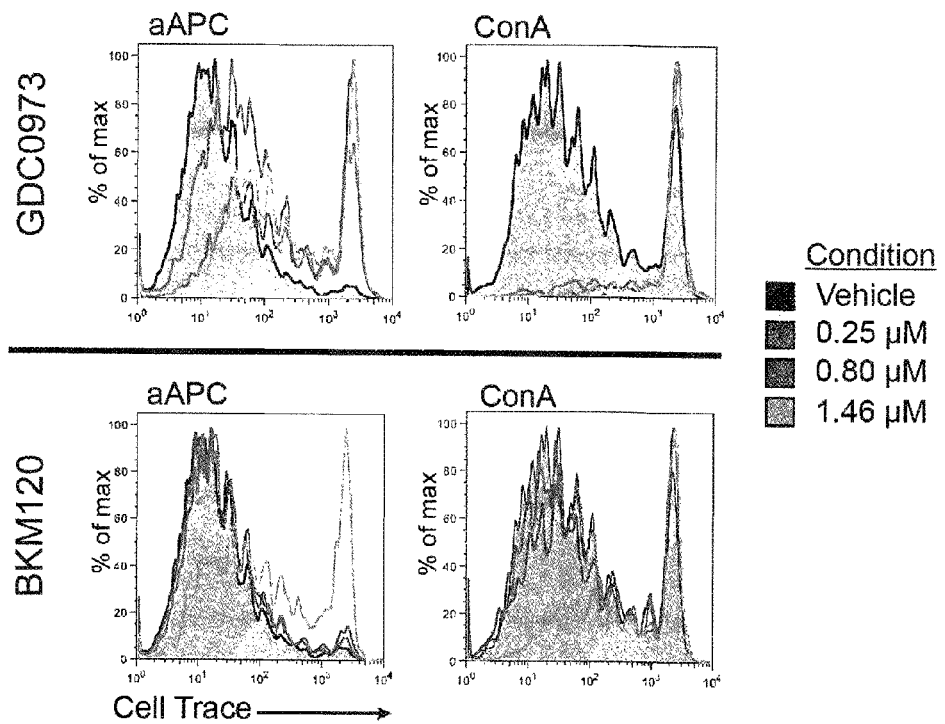
FIG. 1B shows human PBMCs that were stained with CELLTRACE stain and activated with either aAPCs or ConA in the presence of inhibitors. Four plots show proliferation of CD8 cells after 7 days is shown.
Figure 1C:
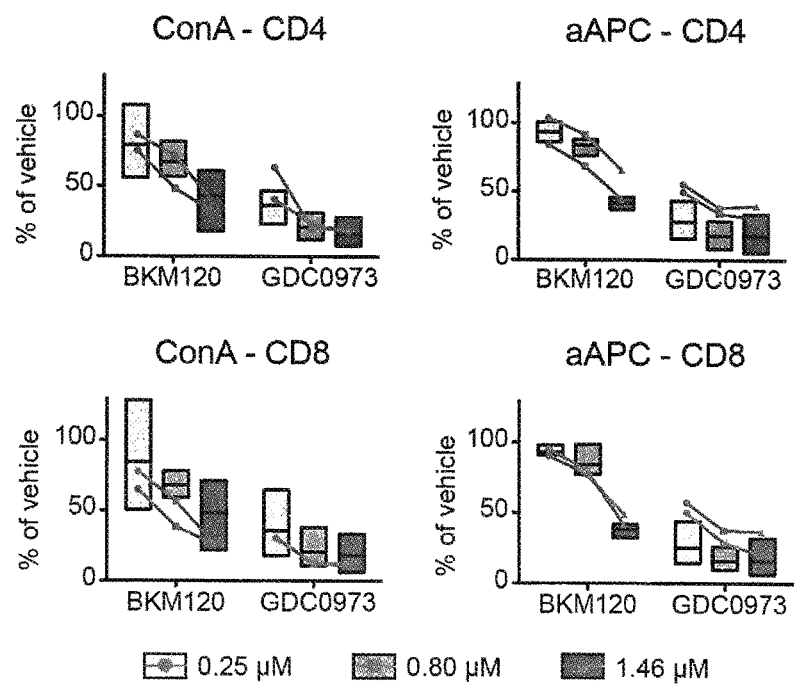
FIG. 1C shows quantifications of the division index normalized to vehicle for CD4 and CD8 T cells. Four box plots show mean, min, and max from three experiments with cells from a single donor, and red lines show values from single experiments with two additional donors.
Figure 1D:
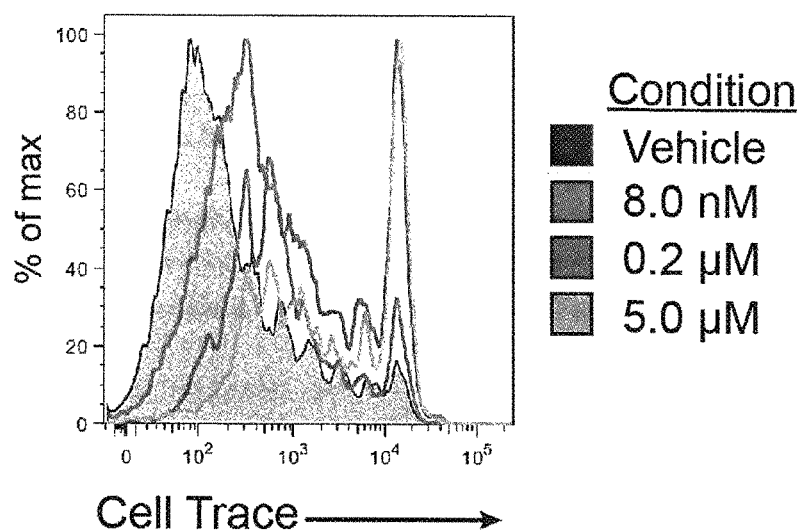
FIG. 1D is a trace showing proliferation of CD8 cells after 7 days with trametinib.
Figure 8:
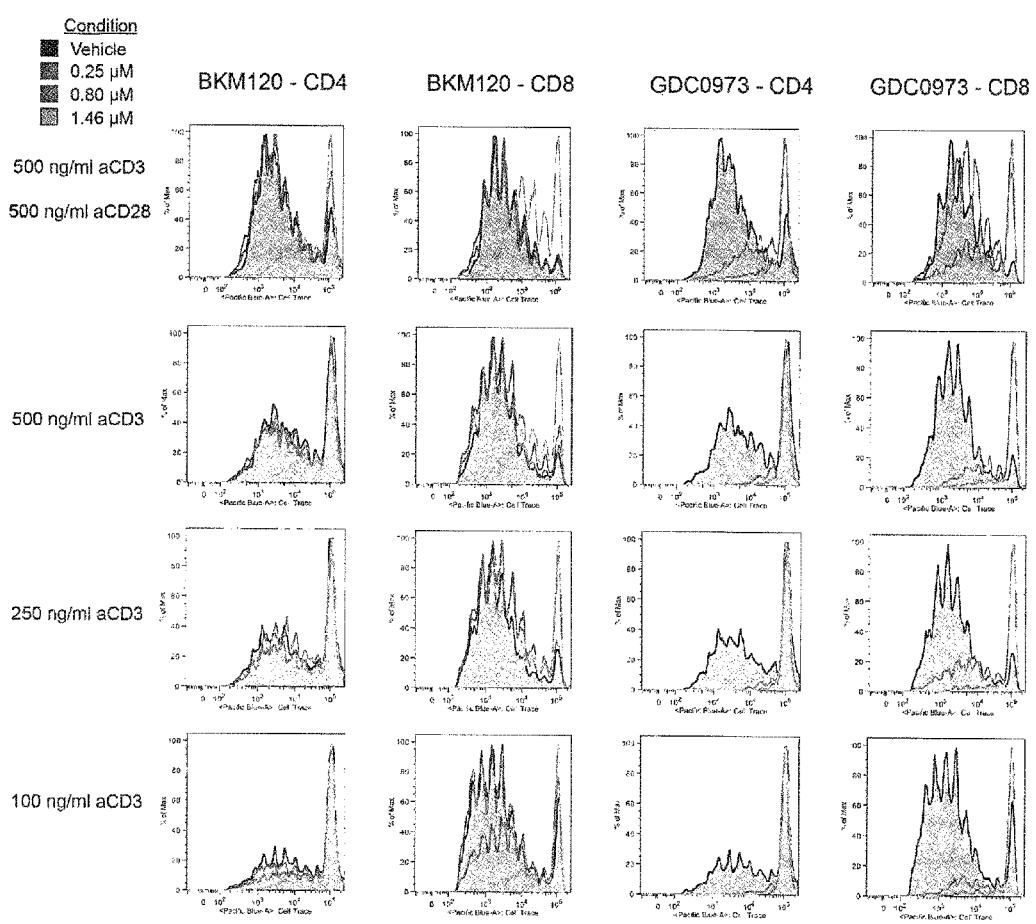
FIG. 8 illustrates in 16 plots that stimulation strength affects T cell sensitivity to PI3K and MEK inhibitors. Human PBMCs were stained with CELLTRACE and activated with either aAPCs loaded with anti-CD3 and anti-CD28 or anti-CD3 alone at various concentrations in the presence of inhibitors. Proliferation of CD8 and CD4 cells after 7 days is shown.

We validated our screening approach by focusing on inhibitors of the PI3K and MEK signaling pathways. Abrogation of T cell activation elicited by targeted inhibitors was not restricted to ConA stimulation because pan-PI3K (BKM120) and MEK (GDC0973) inhibitors also restricted the proliferation of human T cells in response to artificial antigen presenting cells (aAPC) coated with agonistic CD3 and CD28 antibodies[15] (FIG. 1B). Importantly, these effects were consistent among 3 different donors (FIG. 1C). Comparable results were obtained with the MEK inhibitor trametinib (FIG. 1D). As expected, T cells were more sensitive to the kinase inhibitors when they were stimulated with weaker signals (aAPCs lacking anti-CD28 and lower concentrations of anti-CD3, as could occur in tumor-bearing hosts (FIG. 8).

Figure 1E:
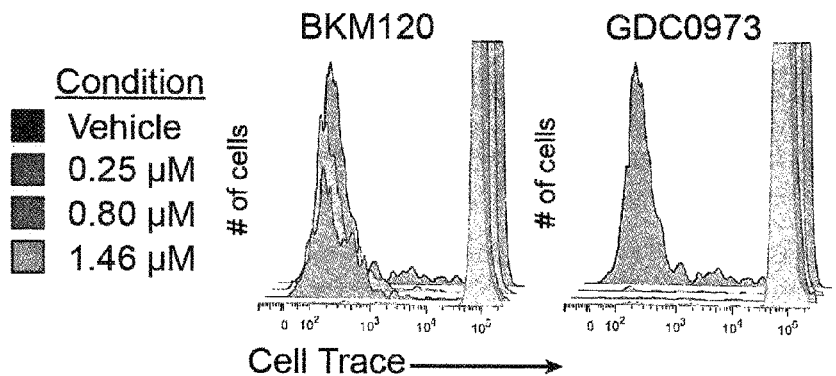
FIG. 1E are two traces of mouse splenic T cells that, primed with tumor antigen, pulsed DCs in the presence of the inhibitors.
Figure 1F:
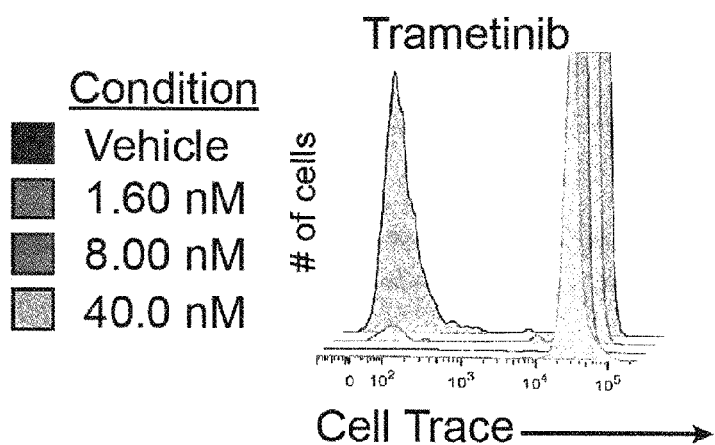
FIG. 1F is a trace showing proliferation of CD8 cells after 7 days is shown.
Figure 1G:
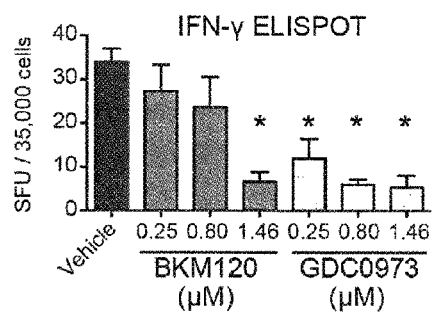
FIG. 1G is a bar graph showing mouse splenic T cells that were primed with tumor antigen and pulsed DCs for 7 days.
Figure 1H:
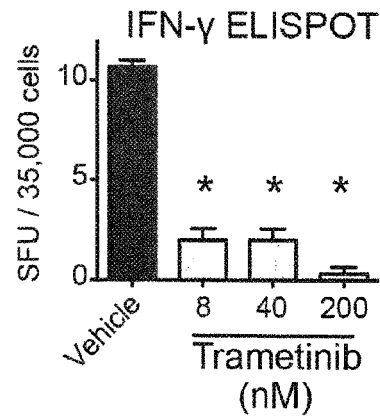
FIG. 1H is a bar graph showing that the cells of FIG. 1G were then recalled with fresh tumor antigen pulsed DCs in the presence of inhibitors in an IFN-γ ELISpot. *=P<0.05, unpaired t-test.

Consistent with these findings, active doses of the pan-PI3K and MEK inhibitors completely abrogated the initial priming response of murine T cells activated with tumor lysate-pulsed dendritic cells (DCs)[16,17] (FIGS. 1E and 1F). More importantly, the direct suppressive effects of pan-PI3K and MEK inhibitors were not restricted to proliferative responses because the frequency of murine tumor-primed T cells secreting IFN-γ in response to re-stimulation with fresh tumor lysate-pulsed DCs was also significantly reduced when either pan-PI3K or MEK were inhibited (FIGS. 1G and 1H).

Figure 9A:
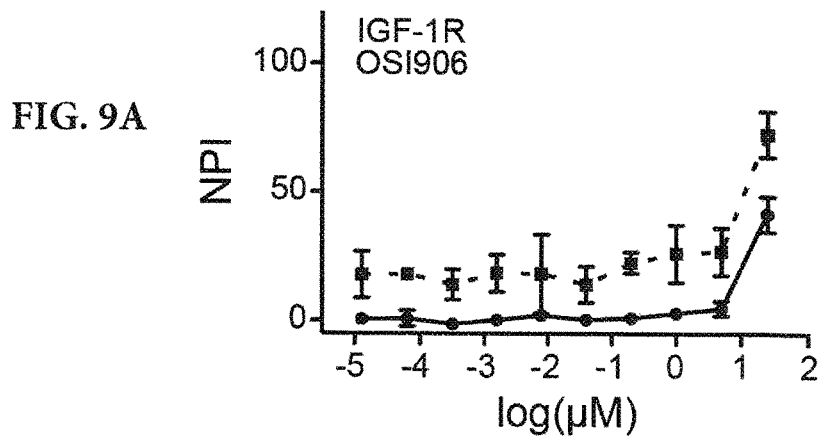
FIG. 9A illustrates that OSI906 preserves T cell function at the concentrations required to inhibit MCF-7 cells. A2780 cells cultured for 3 days and human T cells activated with ConA for 7 days with the IGF-1R inhibitor OSI906. Plot shows NPI vs. concentration.
Figure 9B:
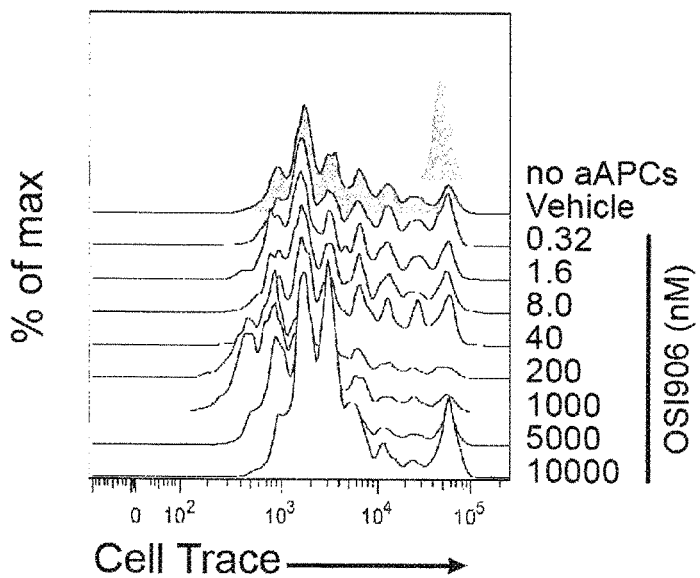
FIG. 9B shows that human PBMCs were stained with CELLTRACE reagent and activated with aAPCs in the presence of OSI906. Proliferation of CD8 cells after 7 days is shown.
Figure 9C:
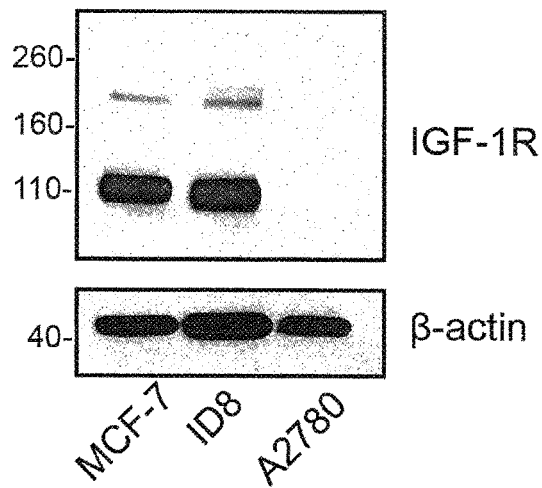
FIG. 9C shows that human A2780 and MCF-7 cells and murine ID8 cells were blotted for IGF-1R expression.
Figure 9D:
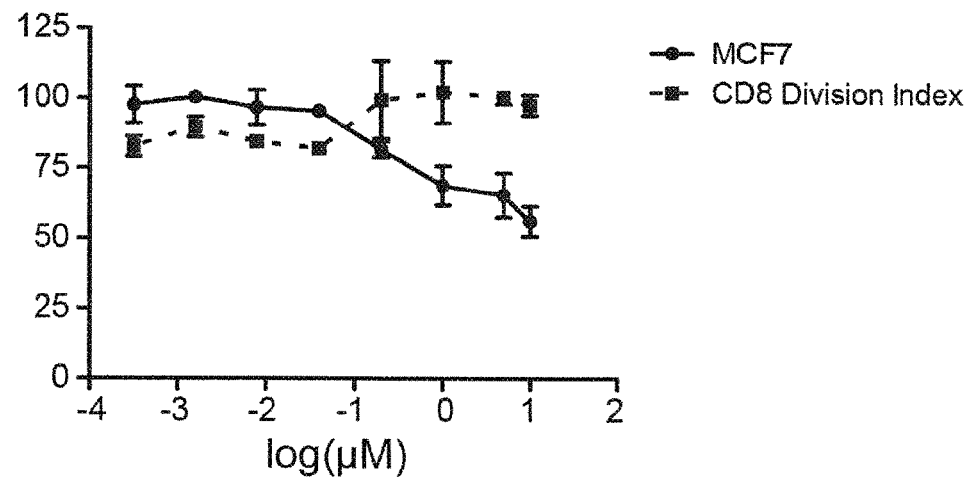
FIG. 9D shows the division indices of CD8 T cells from the experiment described in FIG. 9B are plotted relative to vehicle treatment alongside the proliferation of MCF-7 cells treated with OSI906 for 2 days, measured by percent of vehicle in an MTS assay. Representative results from one of two independent experiments.
Figure 9E:
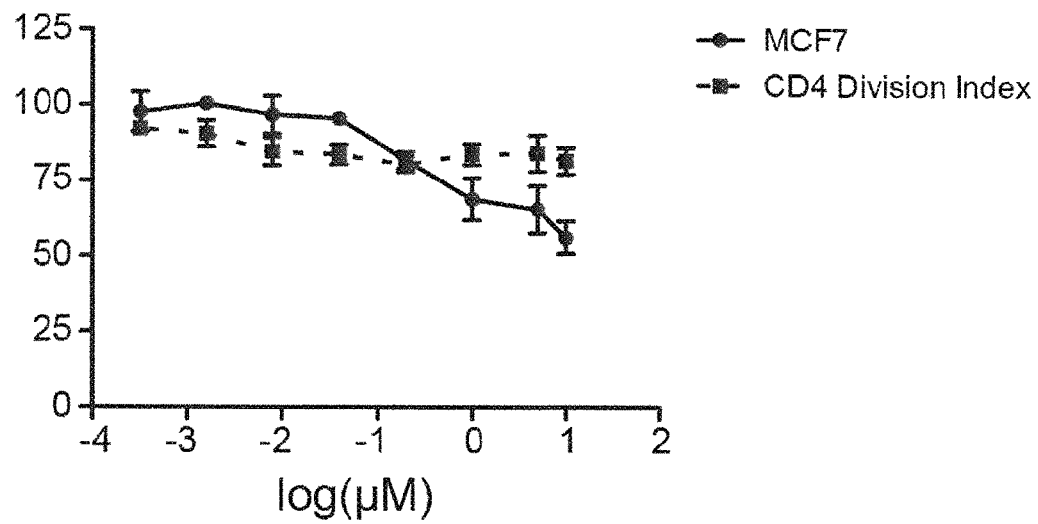
FIG. 9E shows the division indices of CD4 T cells from the experiment described in FIG. 9B are plotted relative to vehicle treatment alongside the proliferation of MCF-7 cells treated with OSI906 for 2 days, measured by percent of vehicle in an MTS assay. Representative results from one of two independent experiments.

One inhibitor from our panel, OSI906 that targets the IGF-1R, did not show any activity on T cells or A2780 cells (FIG. 9A and Table 1), except at a high concentration that may allow off-target inhibition of other kinases. We confirmed that it also did not impact aAPC-induced T cell proliferation (FIG. 9B), and that A2780 cells were resistant to OSI906 likely because they do not express the IGF-1R (FIG. 9C). When we measured the activity of OSI906 on MCF-7 tumor cells, which express the IGF-1R (FIG. 9C) and are sensitive to IGF-1R signaling blockade[18], we achieved a reduction in tumor cell proliferation at concentrations that did not affect T cells (FIGS. 9D and 9E), suggesting that therapeutic targeting of IGF signaling can be achieved with minimal side effects on T cells. Together, these results indicated that many small molecule inhibitors targeting pathways shared by tumor cells and activated T lymphocytes impair T cell expansion and the production of effector cytokines at doses required for anti-tumor activity in vitro.

EXAMPLE 3: IL-15 Rescues T Cells from MEK Inhibition through PI3K Activation

Figure 2A:
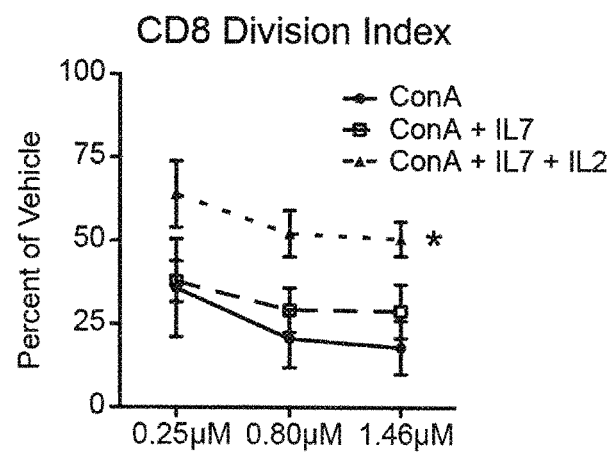
FIG. 2A is a graph showing that IL-15 can rescue T cell functions from MEK inhibitors. A proliferation of human PBMCs activated with ConA+/−IL-2 (20 U/ml) and IL-7 (2 ng/ml) was quantified with the division index and plotted as percent of the corresponding vehicle treatment for each group. Averages from 3 independent experiments. *=P<0.05 t-test vs ConA only.
Figure 2B:
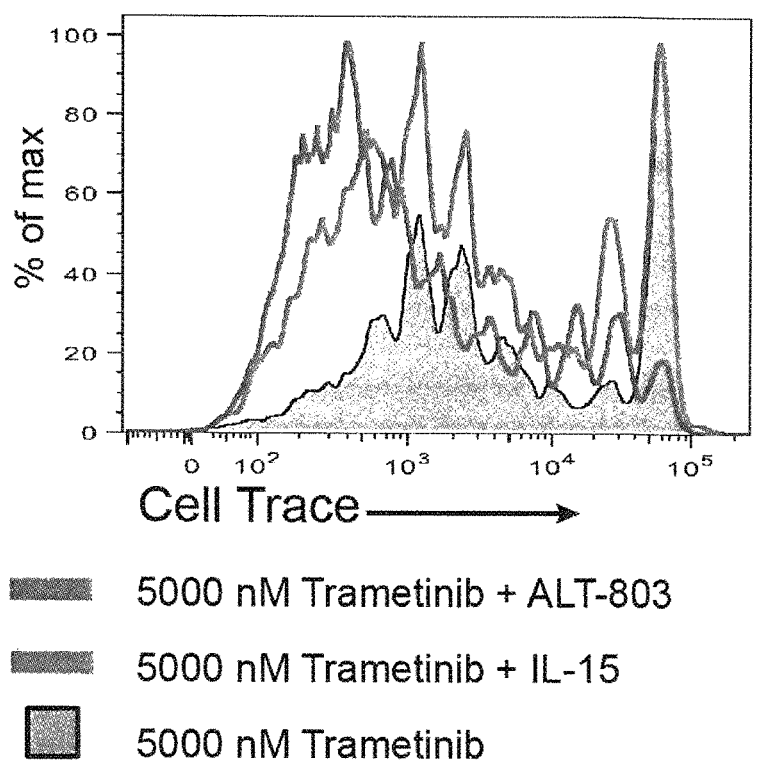
FIG. 2B shows human PBMCs stained with CELLTRACE stain and activated with aAPCs+/−IL-15 (10 ng/ml) or ALT-803 (35.7 ng/ml) in the presence of trametinib. Proliferation of CD8 T cells after 7 days is shown.

Because trametinib is approved for clinical use, we were particularly interested in whether methods to selectively rescue T cells from potent MEK inhibition could improve the therapeutic efficacy of trametinib. We therefore tested a panel of T cell survival and/or proliferation cytokines on their ability to recover T cell expansion from MEK inhibition. While IL-21 and IL-27 had no effect, IL-7, IL-2, and IL-15 were all able to rescue T cell proliferation in the presence of the MEK inhibitors, although to differing degrees (FIGS. 2A, 2B and 10). We focused on IL-15 because it provides strong memory signaling to CD8 T cells without inducing Treg expansion, as compared to IL-2[19,20].

We found that IL-15 can rescue early (within 10 minutes) TCR-induced MAPK signaling from MEK inhibition, as shown by ERK1/2 phosphorylation (FIG. 2C). Mechanistically, this effect depends on the activation of the PI3K pathway by IL-15[21], because IL-15 was unable to rescue the defect in ERK phosphorylation in the presence of the pan-PI3K inhibitor BKM120. Furthermore, activation of protein kinase C (PKC) with phorbol-12-myristate-13-acetate (PMA) completely overcomes the suppressive effect of PI3K inhibition on ERK phosphorylation without fully restoring AKT phosphorylation. These data are consistent with a mechanism of ERK phosphorylation[22] mediated by the activation of PKC isoforms upon stimulation of the PI3K pathway, which is known to result in the production of phosphatidylinositol (3,4,5)-trisphosphate (PIP3) and, subsequently, activation of the PDK1 kinase[23]. As expected, this PI3K-dependent rescue by IL-15 was also apparent in our T cell activation experiments, as T cell expansion could not be fully rescued when PI3K and MEK inhibitors were combined (FIG. 2D). Together, these results show that IL-15 can augment early signaling events downstream of TCR activation to enhance the amplitude of MAPK signaling to overcome MEK inhibition by trametinib.

Figure 2E:
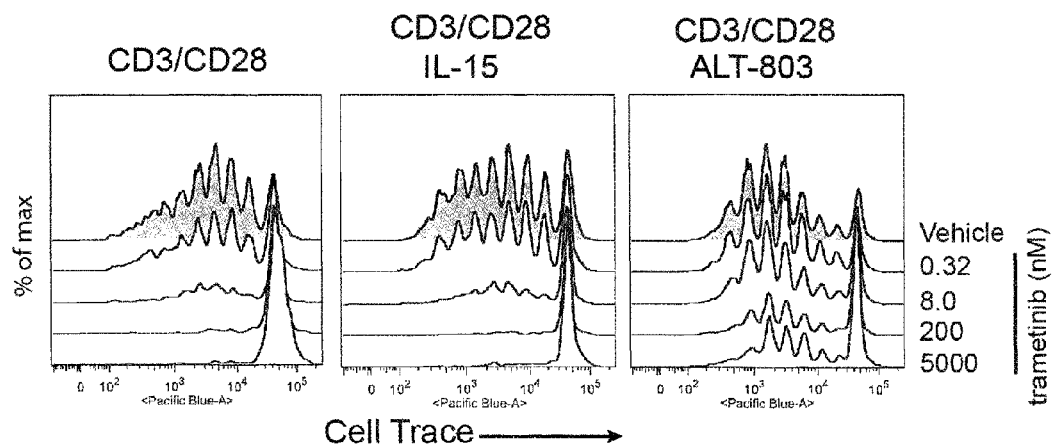
FIG. 2E shows three graphs of mouse T cells isolated from spleens and CELLTRACE stain labeled, then activated with aCD3/aCD28 beads and IL-15 (10 ng/ml) or ALT-803 (35.7 ng/ml) for 3 days with trametinib. Proliferation of CD8 T cells is shown.
Figure 2F:
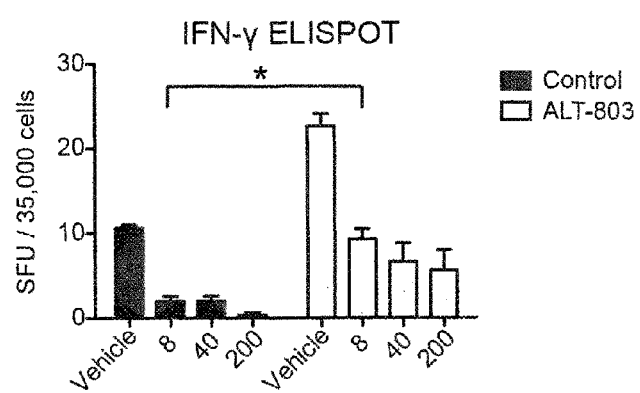
FIG. 2F shows mouse splenic T cells that were primed with tumor antigen-pulsed DCs for 7 days and then recalled with fresh tumor antigen-pulsed DCs in the presence of trametinib+/−ALT-803 (35.7 ng/ml) in an IFN-γ ELISpot assay. *=P<0.05

EXAMPLE 4: Combination of IL-15 Agonists and Trametinib Induces Rejection of KRas-Mutated Tumors To define whether IL-15 signaling can overcome MEK inhibition-induced suppression of T cell activation in vivo in the tumor microenvironment, we used the IL-15 superagonist ALT-803[24], which was more effective than IL-15 at rescuing both human and mouse T cell proliferation at equimolar concentrations in vitro (FIGS. 2B, 2D, and 2E), and also restored the IFN-γ recall response of tumor-primed T cells in the presence of trametinib (FIG. 2F).

Figure 2G:
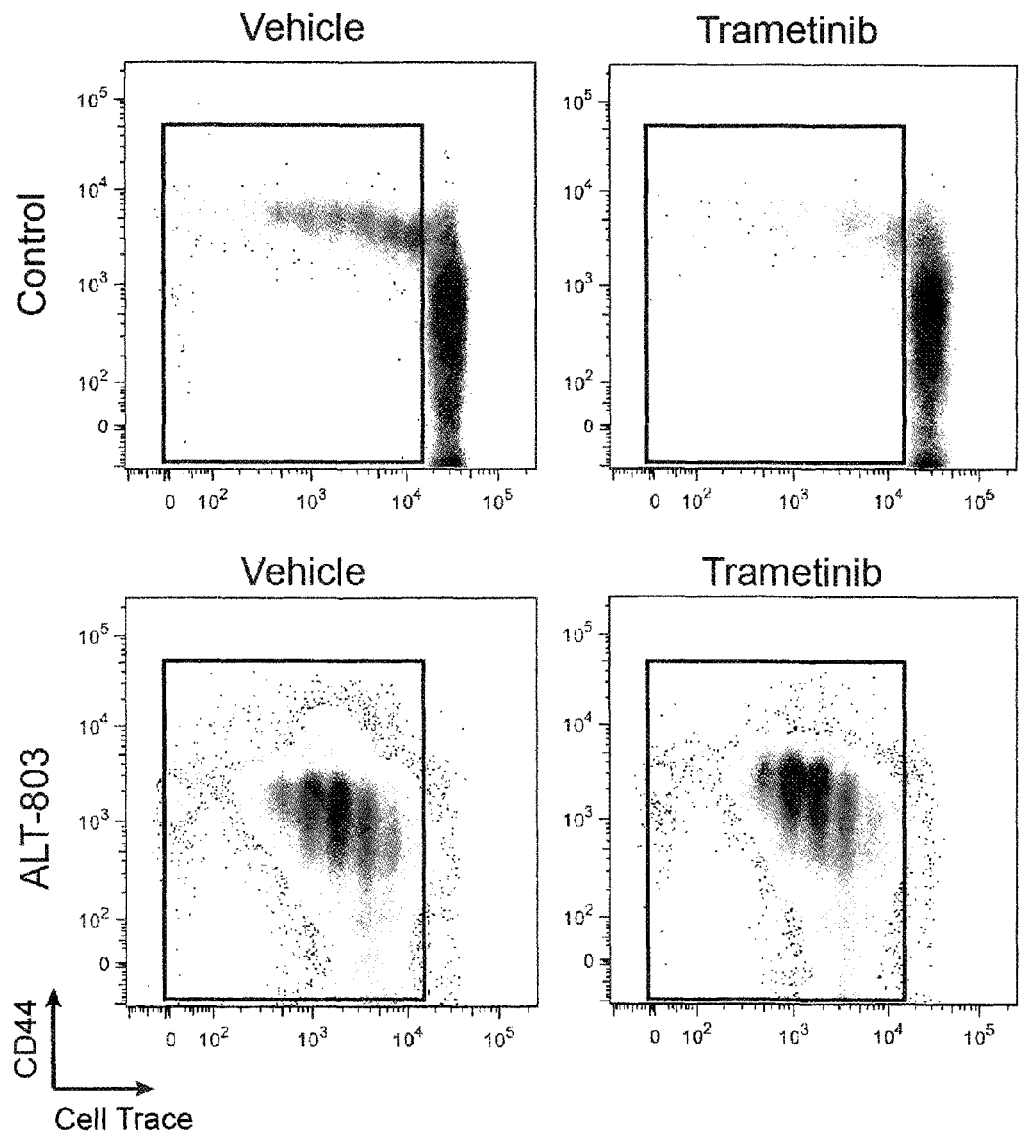
FIG. 2G shows mice that were injected with ID8-OVA cells, treated with trametinib (1.0 mg/kg) or vehicle+/−ALT-803 (0.2 mg/kg), and injected with CELLTRACE-labelled OT-I T cells as described in Example 1. After 4 days, cells were harvested and analyzed for proliferation.
Figure 2H:
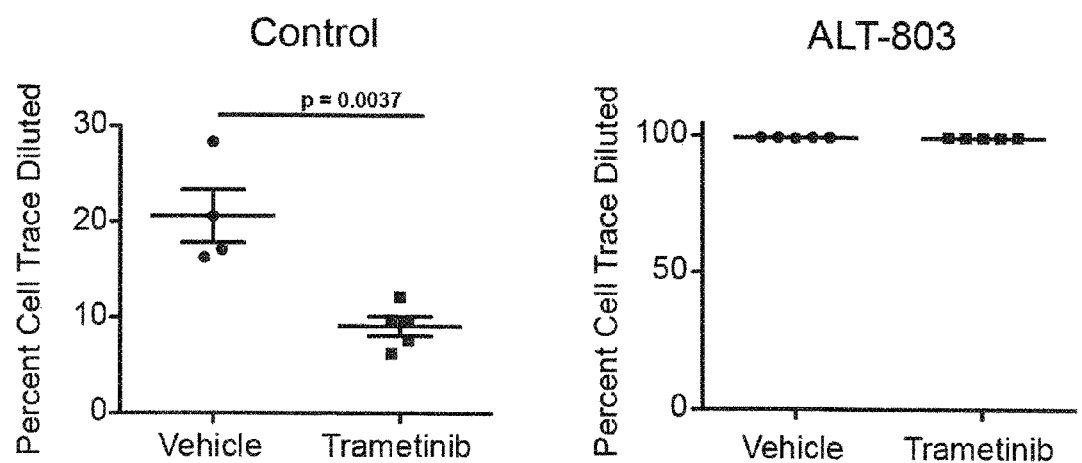
FIG. 2H shows quantification of the percent of OT-I T cells from FIG. 2G that divided.

To test the activity of ALT-803 in the tumor microenvironment, we transferred CELLTRACE Violet-labelled (Ovalbumin (OVA)-specific) OT-I T cells into mice growing OVA-transduced syngeneic ID8 ovarian tumors, a system that allows the recovery of tumor microenvironmental lymphocytes through peritoneal wash[25,26]. After 4 days, we found that in mice treated with trametinib, the OT-I T cells proliferated significantly less than in mice gavaged with vehicle (FIGS. 2G and 2H). Importantly, when ALT-803 was co-administered with the OT-I T cells (only one dose), proliferation was dramatically enhanced and was not restricted by trametinib, indicating that therapeutic activation of IL-15 signaling can restore CD8 T cells suppressed by trametinib in vivo.

Figure 3A:
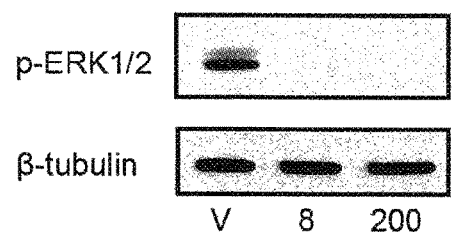
FIG. 3A illustrates that combination therapy with trametinib and ALT-803 can drive rejection of a murine KRas-mutated breast tumor cell line. Brpkp110 cells were cultured with vehicle, 8 nM, or 200 nM trametinib and analyzed by Western blot.

To investigate the therapeutic potential of combining trametinib and ALT-803 against established KRas-mutated tumors, we utilized syngeneic tumor cells derived from an autochthonous breast cancer initiated in triple transgenic (L-Stop-L-KRas$^{G12D}$p53$^{flx/flx}$L-Step-L-Myristoylated p110α) mice with adenovirus-Cre[27-29]. We chose this cell line, termed breast-p53-KRas-p110alpha (Brpkp110), to model treatment against tumors that evade single molecule targeting of the MAPK pathway through activation PI3K signaling, as has been commonly reported in human cancer cells[30-32]. Brpkp110 cells have identifiable signaling through MEK that can be inhibited with trametinib (FIG. 3A) and generate aggressive tumors when grown subcutaneously.

Figure 3B:
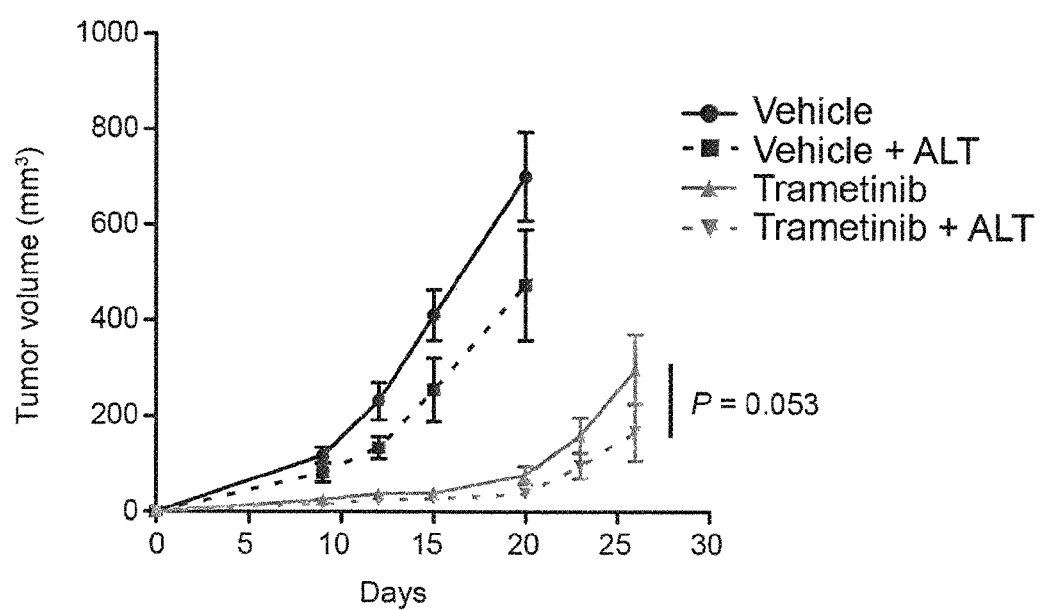
FIG. 3B show mice that were injected with Brpkp110 cells subcutaneously (day 0) and treated once daily with trametinib (1.0 mg/kg) beginning on day 3 until day 13. ALT-803 (0.2 mg/kg) was administered i.p. on days 3, 8, and 13. Combined tumor growth data from two experiments with similar results, n=20 for trametinib and trametinib+ALT-803 groups.
Figure 3C:
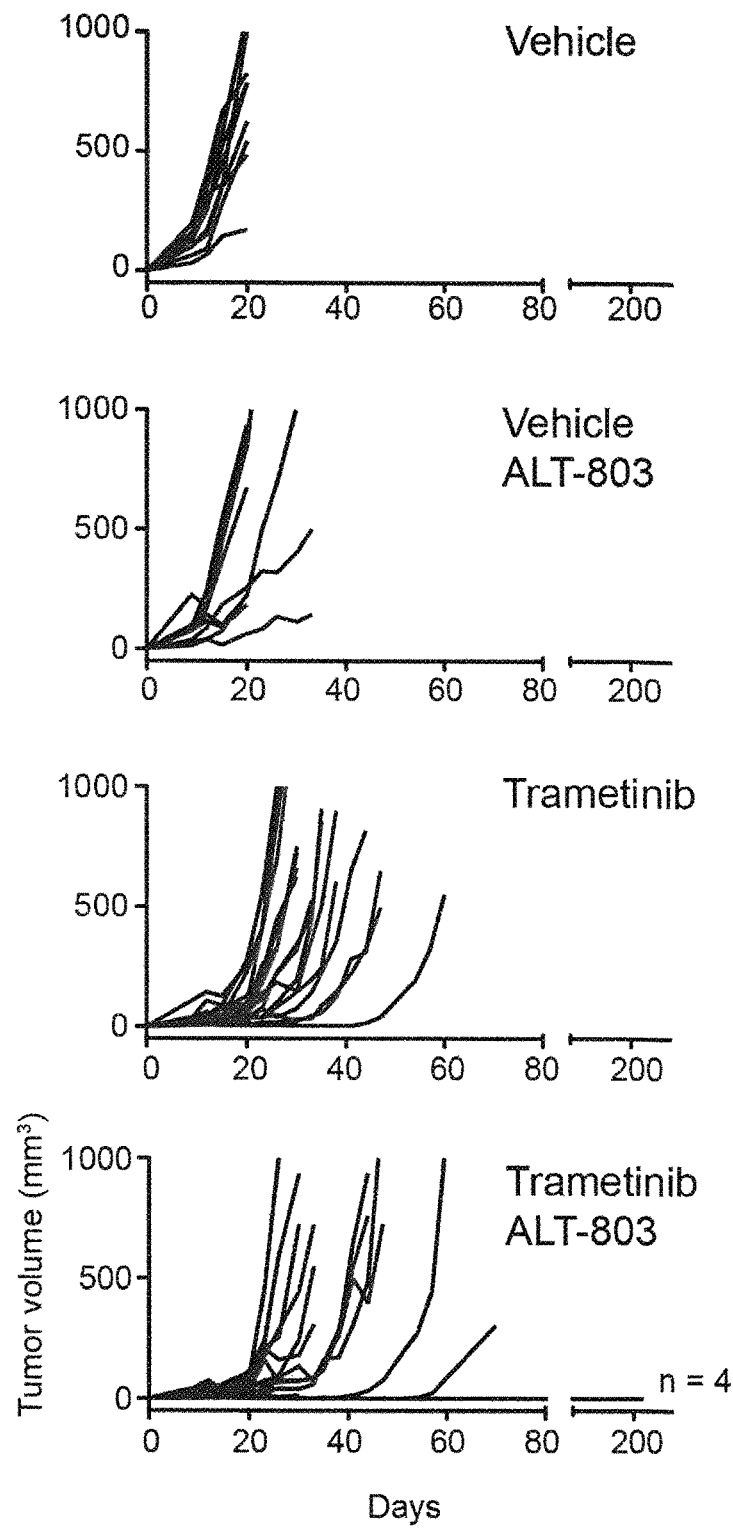
FIG. 3C show four plots showing growth of tumors from individual mice from FIG. 3B.
Figure 3D:
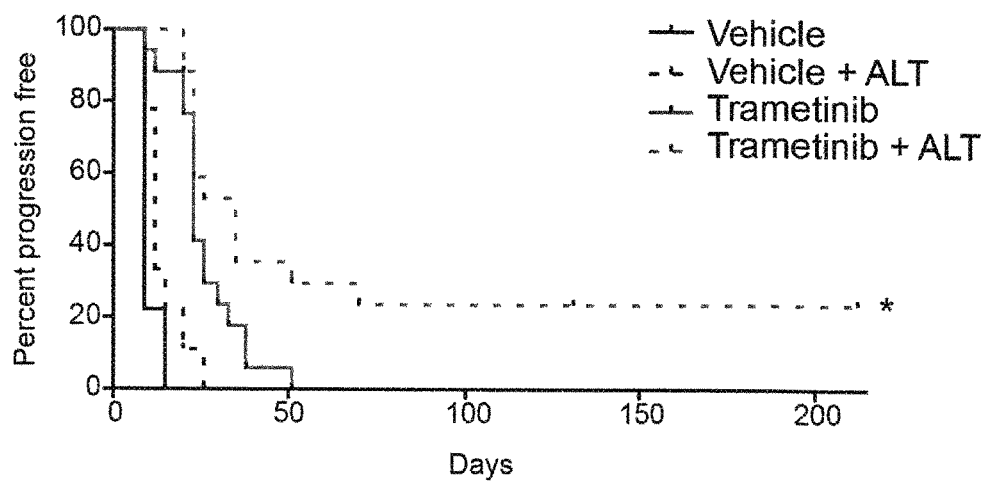
FIG. 3D show plots of percentage of mice with tumors <100 mm$^3$ from FIG. 3B. *Trametinib+ALT survival curve is significant from all other curves, P<0.05 with log-rank test.
Figure 3E:
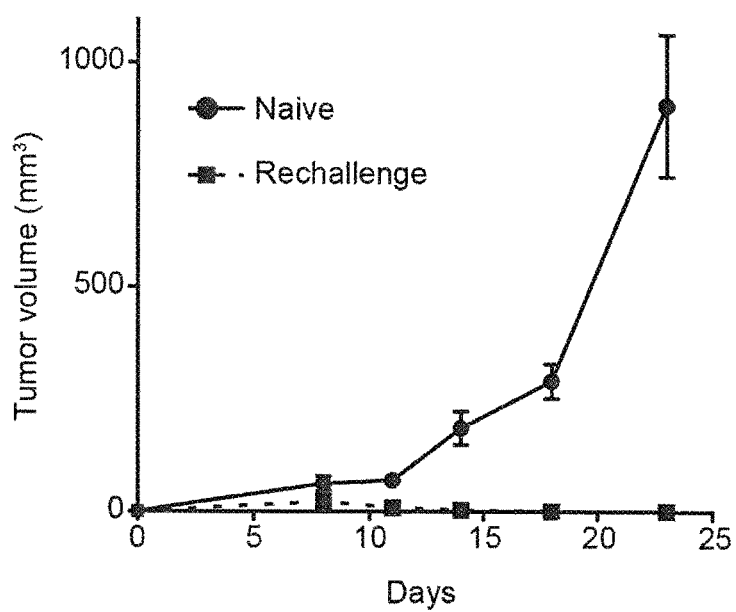
FIG. 3E show mice that had rejected tumors from FIG. 3B were rechallenged about 25 days later with Brpkp110 cells contralaterally and tumor growth was compared to cells injected into naive mice.

Oral gavage with trametinib significantly reduced the growth of Brpkp110 tumors as a single intervention (FIG. 3B), although all mice eventually progressed to terminal disease (FIGS. 3B, 3C, and 3D). In contrast, when ALT-803 was combined during trametinib treatment, Brpkp110 tumors progressed even slower, with 30% of mice remaining tumor free at 50 days, and 20% exhibiting complete rejections in independent experiments. No mice in either single treatment group remained tumor free after 50 days. Most importantly, mice that rejected their tumors in the trametinib/ALT-803 combination group developed immunological memory, because they rejected subsequent re-challenge with Brpkp110 cells in the opposite side over 30 days after initial tumor rejection, whereas naïve control mice developed tumors (FIG. 3E). These results indicate that combining immunostimulatory IL-15 signaling with the anti-tumor activity of trametinib can elicit rejection and prevent recurrence of aggressive tumors through the generation of protective immunity.

Figure 4A:
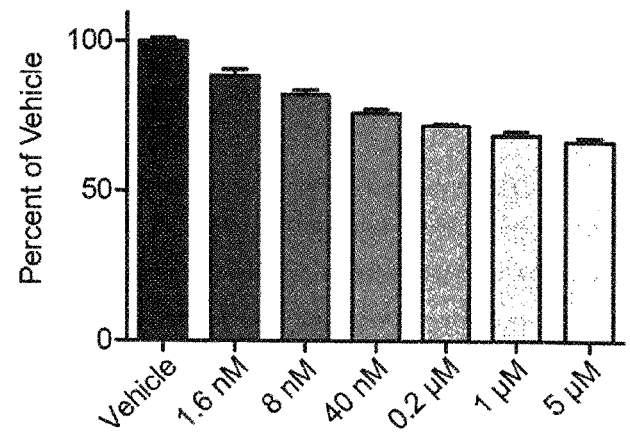
FIG. 4A show that trametinib acts through mechanisms dependent on the microenvironment and CD8 T cells. Brpkp110 cells were cultured for 2 days with trametinib and proliferation was quantified by MTS assay.
Figure 4B:
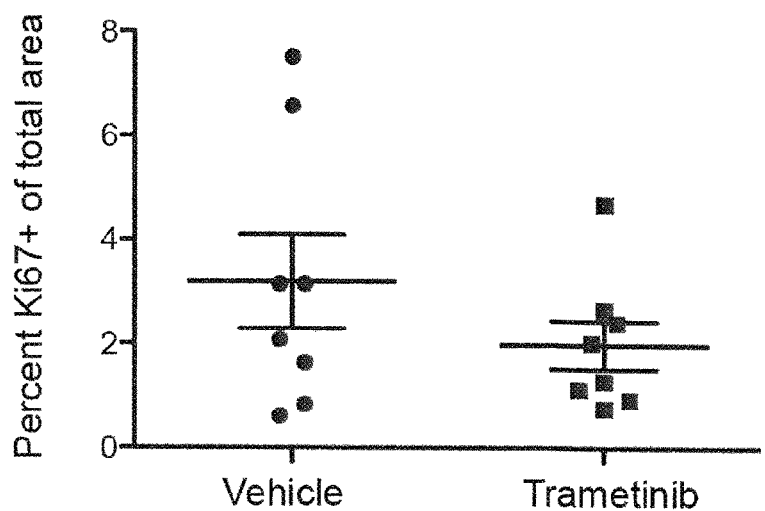
FIG. 4B show that mice with Brpkp110 subcutaneous tumors were gavaged with trametinib (1.0 mg/kg) or vehicle on days 7-9. Tumors were excised on day 10, frozen in OCT, and stained for Ki-67. Positive Ki-67 as % of total tumor area is shown from two experiments.
Figure 4C:
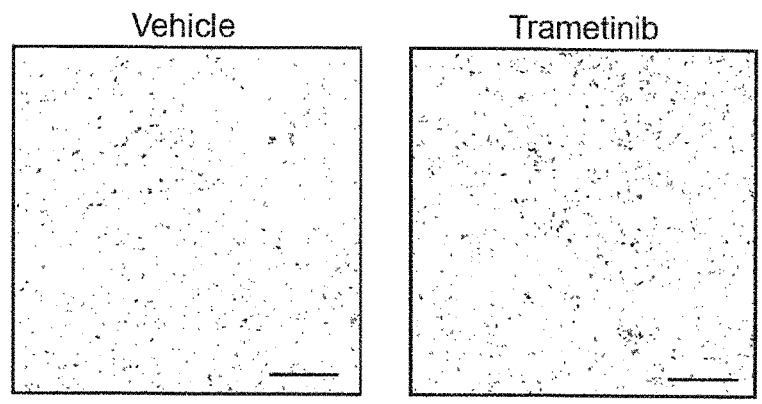
FIG. 4C show images showing positive staining for Ki-67, scale bars=100 μM.
Figure 4D:
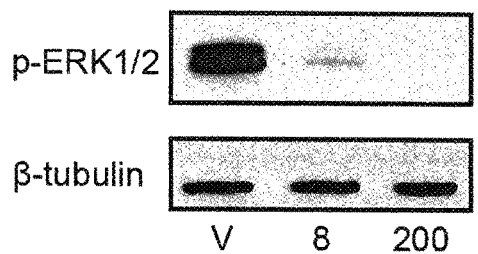
FIG. 4D shows LLC cells that were cultured with vehicle, 8 nM, or 200 nM trametinib and analyzed by Western blot.
Figure 4E:
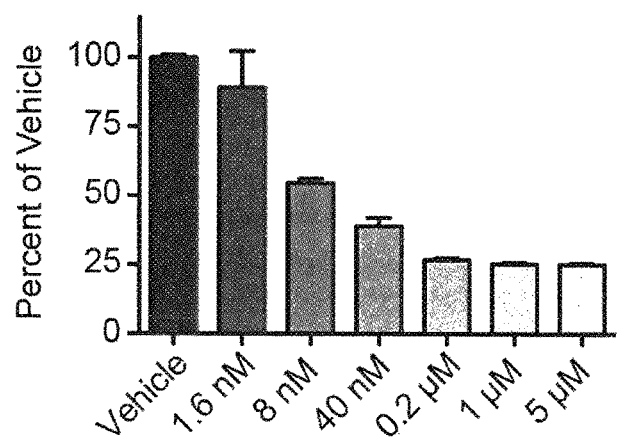
FIG. 4E illustrate that for LLC cells cultured for 2 days with trametinib, proliferation was quantified by MTS assay.
Figure 4F:
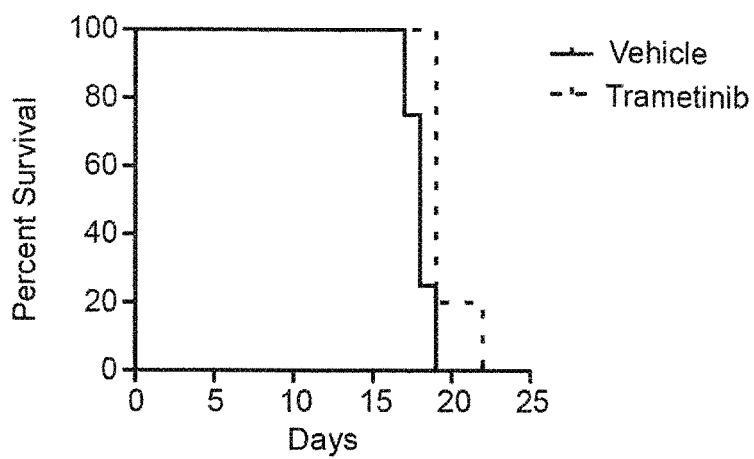
FIG. 4F illustrate mice with intraperitoneal LLC tumors that were gavaged with trametinib once daily from day 4-14.
Figure 4G:
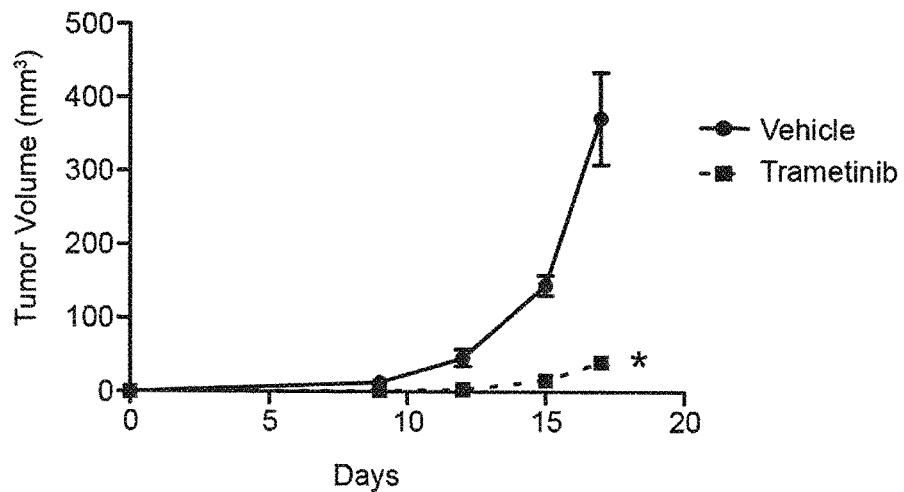
FIG. 4G illustrate mice with subcutaneous LLC tumors that were gavaged with trametinib once daily from day 3-13. P<0.05, Mann-Whitney.

EXAMPLE 5: CD8 T Cells are Required for Optimal Anti-Tumor Activity of Trametinib The significant anti-tumor activity of trametinib as an individual intervention against Brpkp110 tumors was surprising because Brpkp110 cells were only mildly sensitive to trametinib (70% growth compared to vehicle) in multiple independent in vitro cell proliferation assays (FIG. 4A). Accordingly, trametinib did not significantly reduce Ki-67 staining in Brpkp110 tumors in vivo (FIGS. 4B and 4C). Similarly, although Lewis Lung Carcinoma (LLC) cells were very sensitive to trametinib in vitro (FIGS. 4D and 4E), we did not find a reduction in tumor progression when we treated mice harboring intraperitoneal LLC tumors (FIG. 4F). However, supporting that the effects of trametinib primarily depend on non-tumor microenvironmental compartments, when a similar experiment is conducted on mice bearing subcutaneous LLC tumors, trametinib significantly reduced disease progression (FIG. 4G). These results demonstrate that the context of the microenvironment have strong effects on the efficacy of trametinib treatment.

Figure 4H:
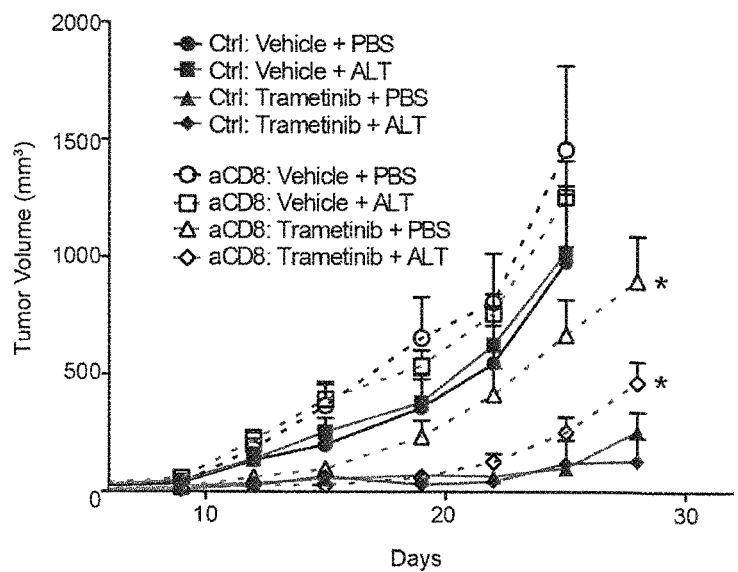
FIG. 4H illustrate that Brpkp110 tumor-bearing mice were treated as in FIG. 4B, except that anti-CD8a or control anti-LTF was also administered. *Tumor volume different from corresponding non-CD8a depleted mice, P<0.05, unpaired t test.
Figure 4I:
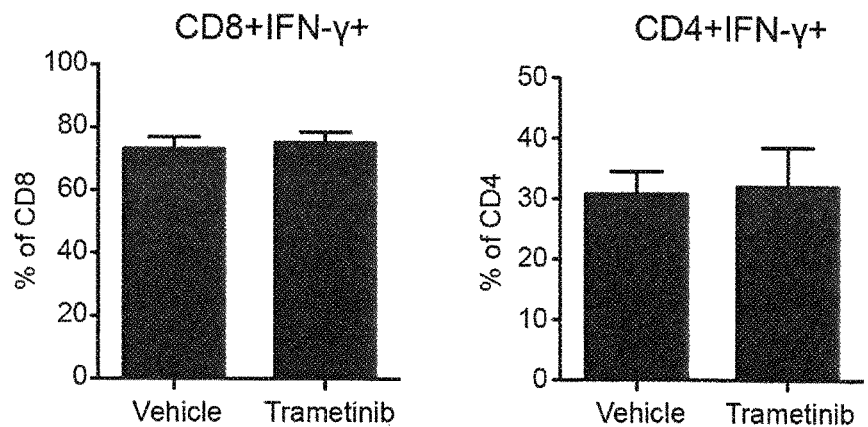
FIG. 4I illustrate mice with Brpkp110 subcutaneous tumors that were gavaged with trametinib (1.0 mg/kg) or vehicle on days 7-9 and harvested on day 10, stimulated with PMA/Ionomycin ex vivo for 5 hrs, and stained for intracellular IFN-γ.

To reconcile the divergent immunological in vitro vs. in vivo effects of trametinib treatment on Brpkp110 growth, we next defined the role of CD8α+ T cells through Ab-mediated depletion. As expected, tumors in mice treated with the trametinib/ALT-803 combination grew significantly faster upon depletion of cytotoxic T cells, compared to identically treated mice receiving an irrelevant IgG (FIG. 4H). Surprisingly, however, and despite its profound T cell suppressive effect in vitro, the anti-tumor activity of trametinib as a single intervention was also significantly reduced in mice depleted of CD8α+ cells. Supporting these data, we found that trametinib treatment of tumor bearing mice did not decrease the frequencies of CD8 or CD4 tumor-infiltrating T cells able to produce IFN-γ when restimulated ex vivo (FIG. 4I). Together, these results support that the therapeutic activity of trametinib is not determined solely by tumor cell intrinsic mechanisms, and that the tumor microenvironment has a large impact on the response to trametinib treatment. Furthermore, irrespective of the degree of cytotoxicity against tumor cells and the suppression of T cells observed in vitro, trametinib requires an intact CD8 T cell compartment for optimal effectiveness against KRas-driven Brpkp110 tumors in vivo.

Figure 5A:
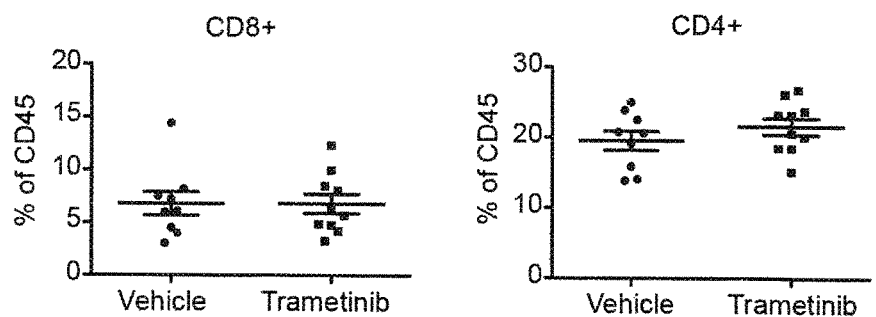
FIG. 5A illustrates that trametinib reduces the accumulation of Ly6C+ MDSCs in tumors. Mice with Brpkp110 subcutaneous tumors were gavaged with trametinib (1.0 mg/kg) or vehicle on days 7-9, harvested on day 10, and analyzed by flow cytometry. Percentages of cell populations found in dissociated tumors from 3 independent experiments.
Figure 5B:
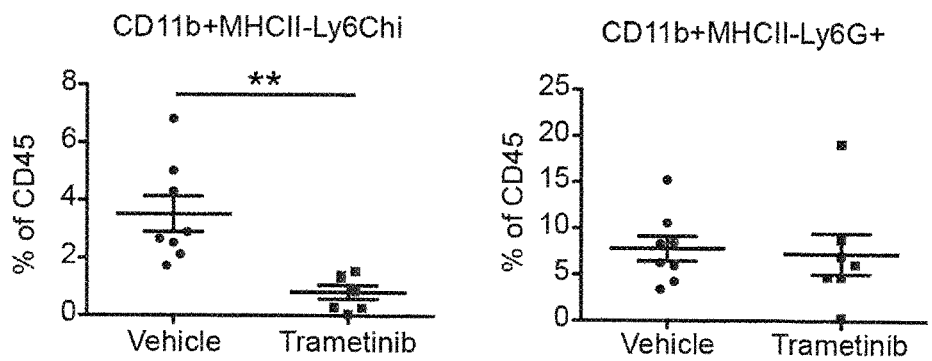
FIG. 5B illustrates that mice with Brpkp110 subcutaneous tumors were gavaged with trametinib (1.0 mg/kg) or vehicle on days 7-9, harvested on day 10, and analyzed by flow cytometry. Percentages of cell populations found in dissociated tumors from 3 independent experiments.
Figure 5C:
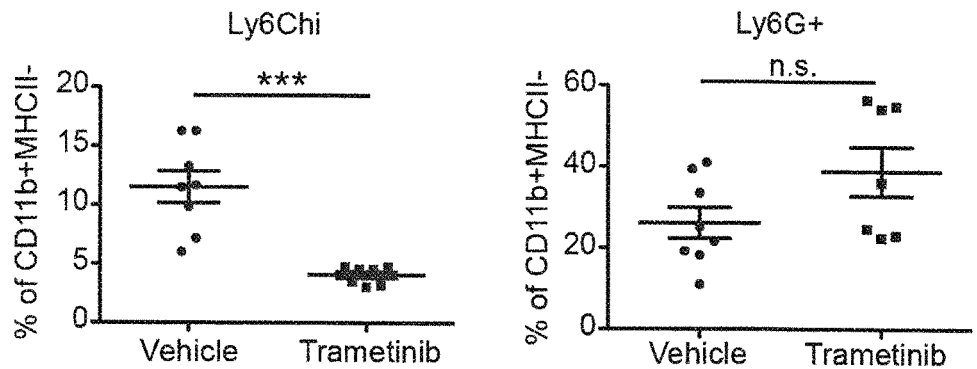
FIG. 5C illustrates that mice with Brpkp110 subcutaneous tumors were gavaged with trametinib (1.0 mg/kg) or vehicle on days 7-9, harvested on day 10, and analyzed by flow cytometry. Percentages of cell populations found in dissociated tumors from 3 independent experiments.
Figure 5D:
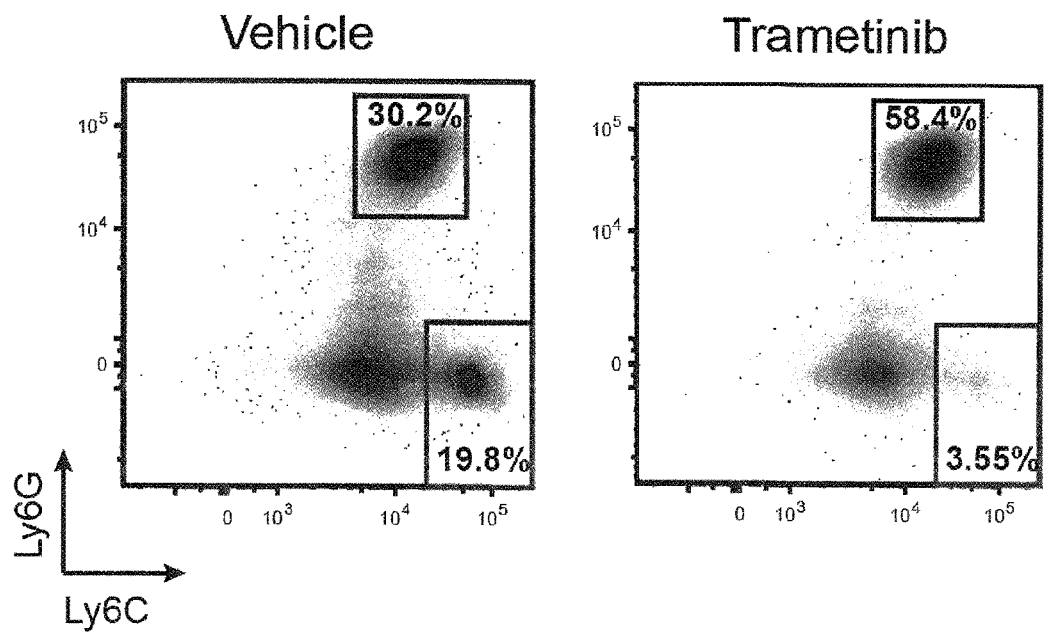
FIG. 5D illustrates the mice with Brpkp110 subcutaneous tumors that were gavaged with trametinib (1.0 mg/kg) or vehicle on days 7-9, harvested on day 10, and analyzed by flow cytometry. This figure shows representative plots of gating for Ly6C$^{hi}$ and Ly6G$^+$ from CD11b$^+$MHCII$^-$ cells in tumors.
Figure 5E:
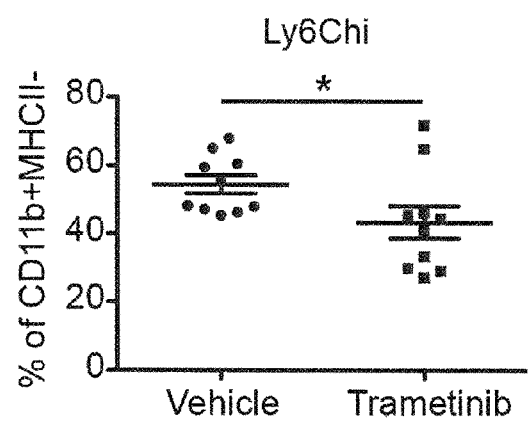
FIG. 5E shows that mice with LLC subcutaneous tumors were gavaged with trametinib (1.0 mg/kg) or vehicle on days 7-9, harvested on day 10, and analyzed by flow cytometry. Percentages of Ly6C$^{hi}$Ly6G$^-$ cells in LLC tumors were from 3 independent experiments.
Figure 5F:
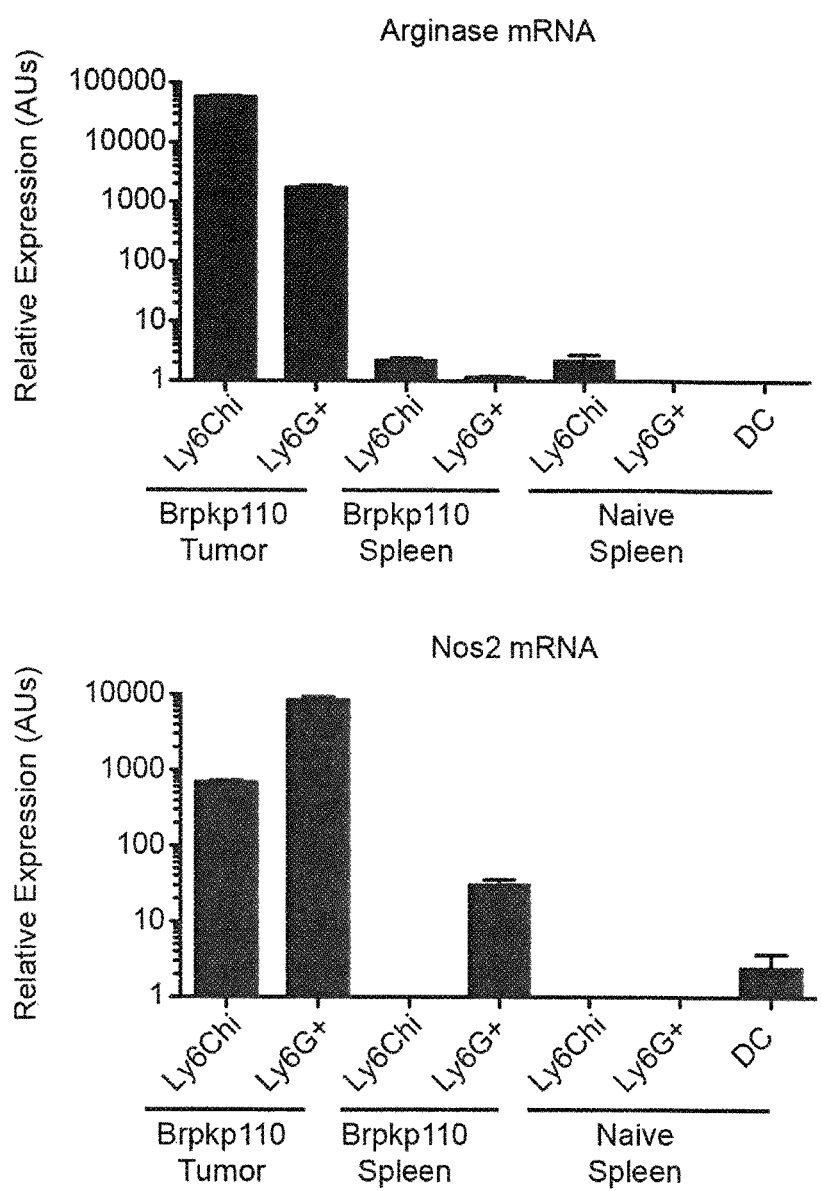
FIG. 5F illustrate in two bar graphs that CD11b$^+$MHCII$^-$ Ly6C$^{hi}$, CD11b$^+$MHCII$^-$ Ly6G$^+$, or CD11c$^+$MHCII$^+$ dendritic cells (DC) were FACS sorted from advanced tumor bearing or naive mice and analyzed by qPCR. Expression normalized to TATA binding protein is shown.
Figure 11A:
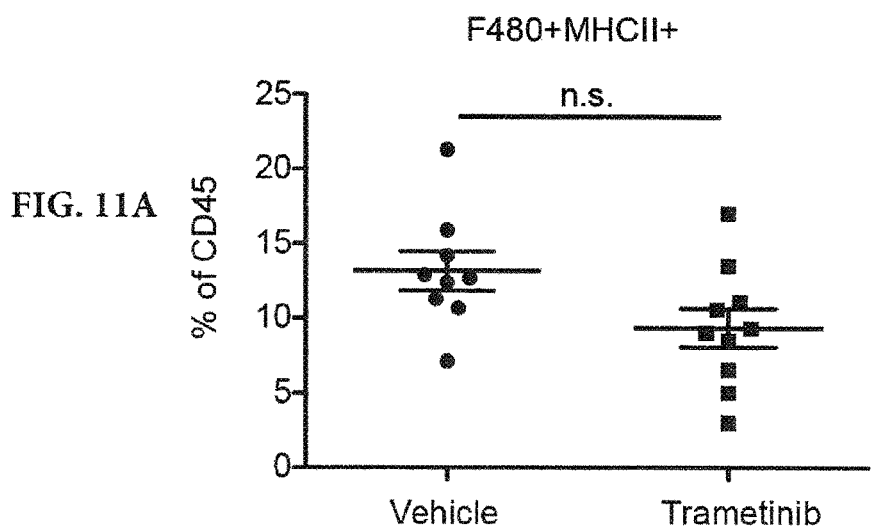
FIGS. 11A, 11B and 11C show that trametinib does not significantly affect macrophage or Treg proportions in Brpkp110 mice. Mice with Brpkp110 subcutaneous tumors were gavaged with trametinib (1.0 mg/kg) or vehicle on days 7, 8, 9 and harvested on day 10 and analyzed by flow cytometry. Percentages of indicated cell populations found in dissociated tumors.
Figure 11B:
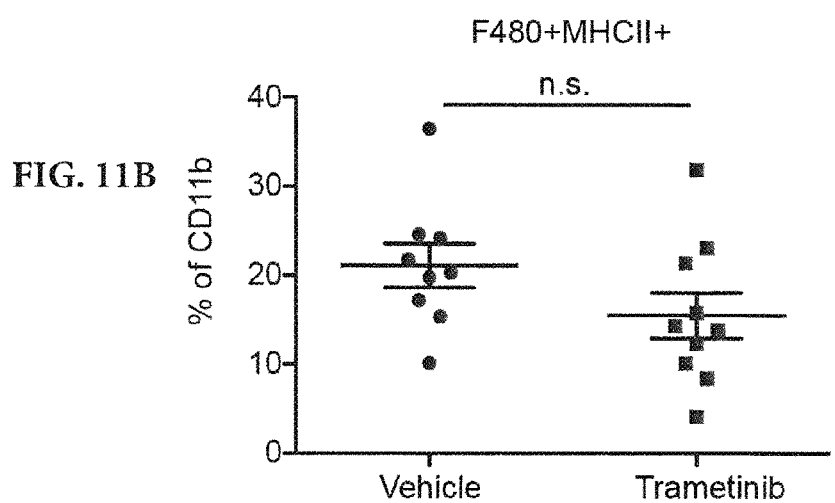
Figure 11C:
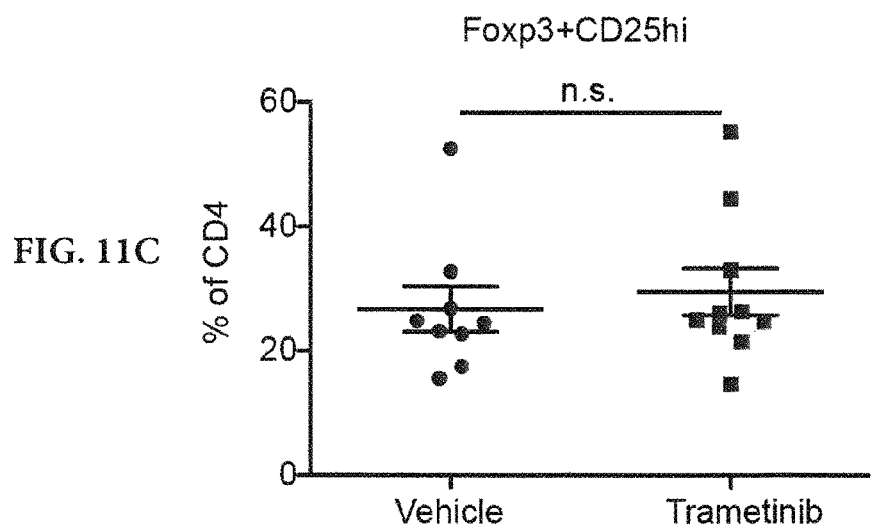

EXAMPLE 6: Trametinib Reduces the Accumulation of Ly6C+ MDSCs in Tumor-Bearing Mice To dissect the effects of trametinib treatment on the microenvironment of Brpkp110 tumors, we treated mice with established tumors for 3 days (to minimize differences in tumor volume) and analyzed the effect on tumor-infiltrating leukocytes. Consistent with a previous report[7], we did not observe a decrease in CD8 or CD4 T cells in trametinib treated mice, supporting that, in vivo, trametinib is not killing or restricting the trafficking of T cells into the tumor (FIG. 5A). The proportion of Foxp3+ Tregs and differentiated (MITC-II+) macrophages also did not significantly change after trametinib treatment (FIG. 11). In contrast, trametinib induced a reproducible reduction in the accumulation of CD11b+MHC-II-Ly6C+Ly6G− (monocytic) MDSCs, while CD11b+MHC-II-Ly6CloLy6G+(granulocytic) MDSCs were surprisingly unaffected, whether analyzed as a proportion of total leukocytes (FIG. 5B), or as a proportion of CD11b+MHC-II-myeloid cells (FIGS. 5C, and 5D). Supporting a broad effect on monocytic MDSCs, corresponding reductions in Ly6C+ MDSCs were found in trametinib-treated, subcutaneous LLC tumors (FIG. 5E). As expected, this MDSC population expresses high levels of the immunosuppressive molecules Arginase1 and Nos2 (FIG. 5F).

Figure 5G:
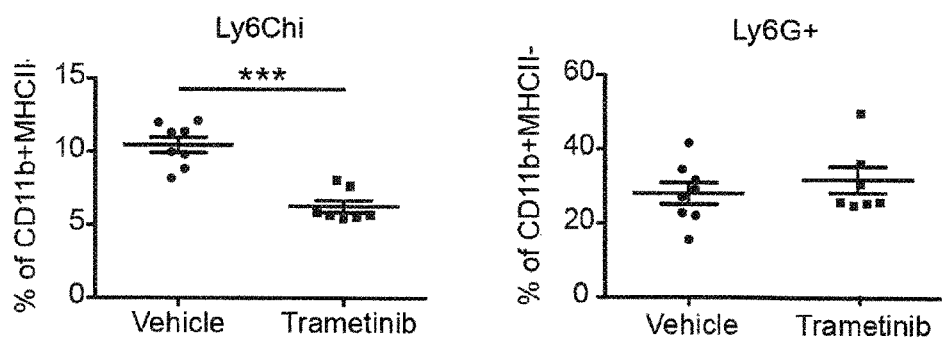
FIG. 5G shows in two charts the percentages or total numbers of cell populations from spleens of Brpkp110 tumor bearing mice of FIG. 5F from one of 3 independent experiments. *p<0.05, p<0.01, *p<0.001, unpaired t test.
Figure 5H:
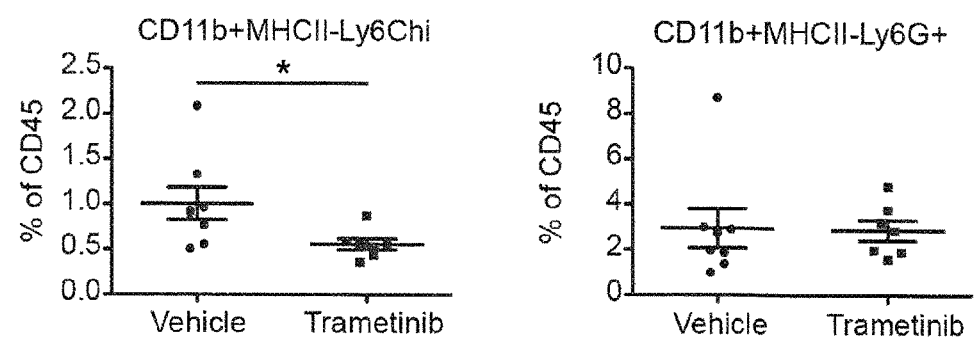
FIG. 5H shows in two charts the percentages or total numbers of cell populations from spleens of Brpkp110 tumor bearing mice of FIG. 5F from one of 3 independent experiments. *p<0.05, p<0.01, *p<0.001, unpaired t test.
Figure 5I:
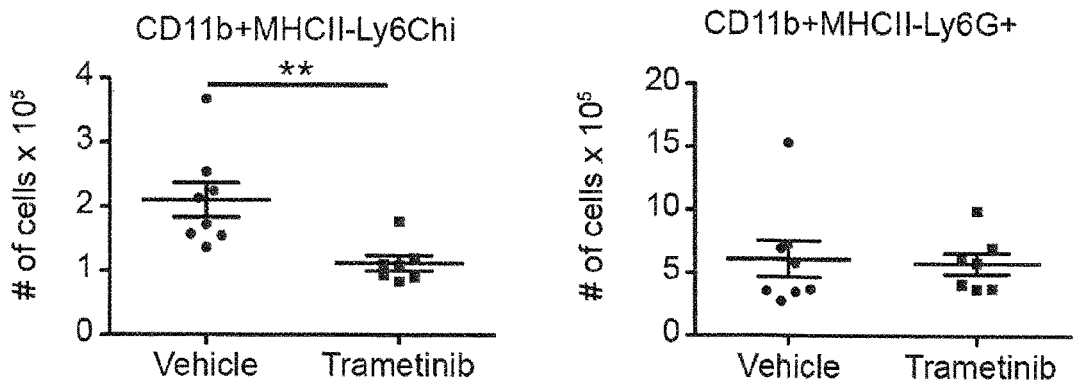
FIG. 5I shows in two charts the percentages or total numbers of cell populations from spleens of Brpkp110 tumor bearing mice of FIG. 5F from one of 3 independent experiments. *p<0.05, p<0.01, *p<0.001, unpaired t test.
Figure 6A:
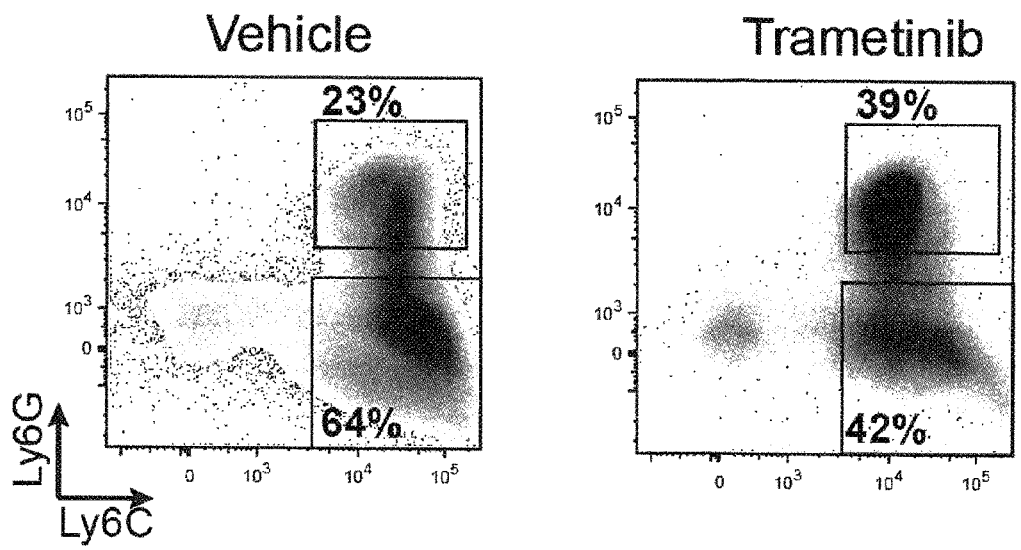
FIG. 6A illustrates that trametinib selectively reduces the differentiation of Ly6C$^+$ MDSCs from bone marrow. MDSCs were differentiated from mouse bone marrow with IL-6 and GM-CSF in the presence of trametinib (200 nM) for 4 days. Shown are representative plots from 4 experiments. *p<0.05, Mann-Whitney test.
Figure 6B:
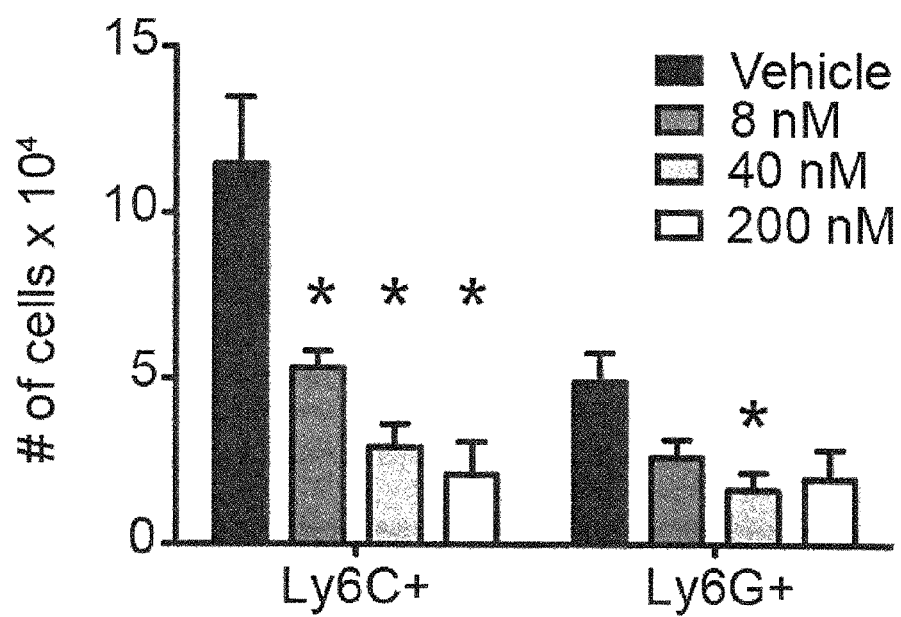
FIG. 6B shows the total number of cells from 4 experiments described as in FIG. 6A. *p<0.05, Mann-Whitney test.
Figure 6C:
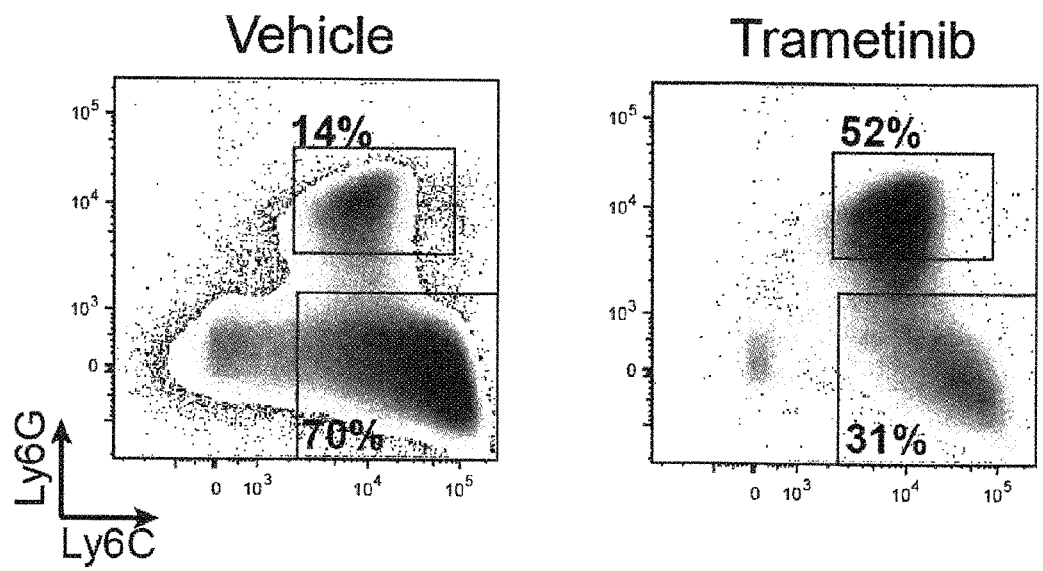
FIG. 6C shows that MDSCs were differentiated from mouse bone marrow with Brpkp110 conditioned medium (50%) in the presence of trametinib (200 nM) or vehicle for 4 days by representative plots from 4 experiments. *p<0.05, Mann-Whitney test.
Figure 6D:
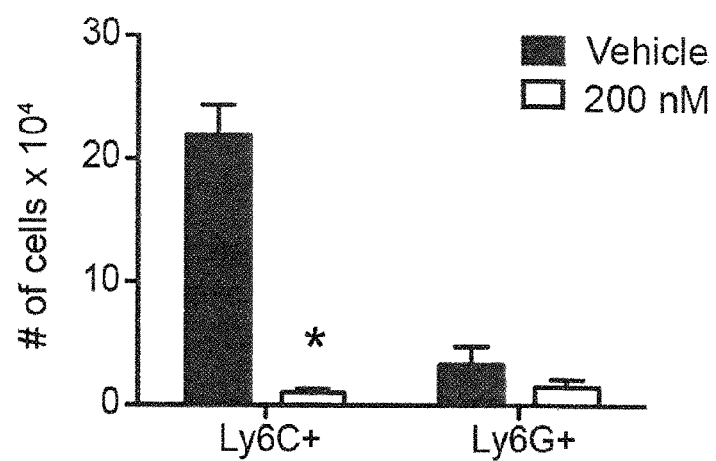
FIG. 6D shows the total number of cells from 4 experiments as described in FIG. 6C. *p<0.05, Mann-Whitney test.
Figure 6E:
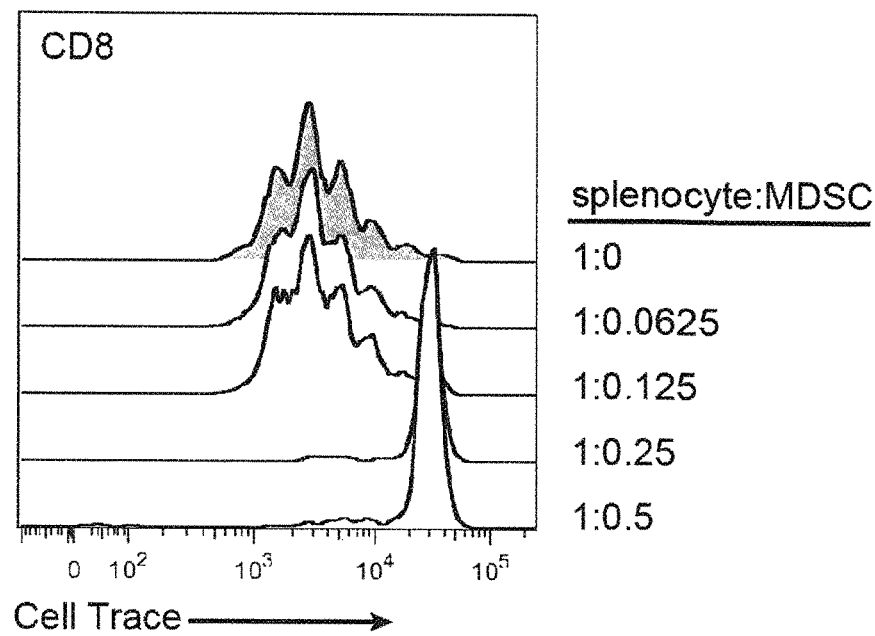
FIG. 6E shows that MDSCs differentiated with Brpkp110 conditioned medium were added to mouse splenocytes activated with anti-CD3 and anti-CD28 and cultured for 3 days.

Notably, this selective reduction in Ly6C+ MDSCs was also observed in the spleens of trametinib treated tumor-bearing mice (FIGS. 5G, 5H, and 5I), suggesting a systemic effect on MDSC mobilization. Supporting these data, trametinib treatment dramatically impaired the differentiation of Ly6C+ MDSCs from bone marrow in response to GM-CSF and IL-6[33], with much weaker effects on Ly6G+ MDSCs (FIGS. 6A and 6B). Similar selective inhibitory effects were observed on MDSCs differentiated with Brpkp110-conditioned media (FIGS. 6C and 6D), which are capable of potently suppressing proliferation of T cells (FIG. 6E).

Figure 6F:
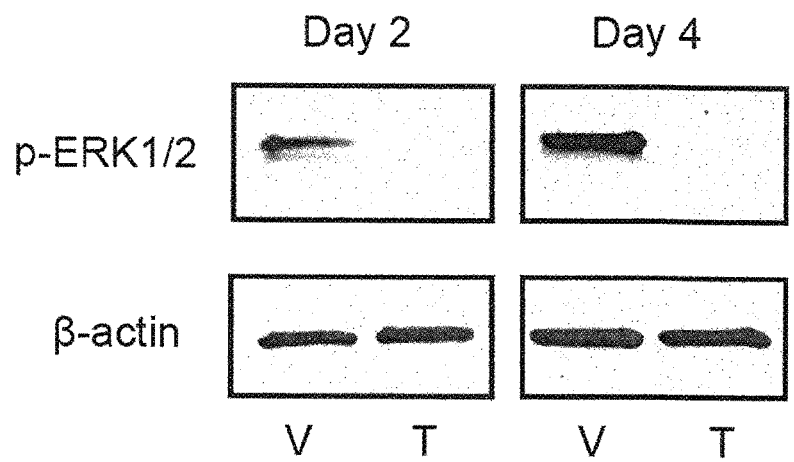
FIG. 6F shows the MDSCs were differentiated as in the experiment described in FIG. 6C and analyzed by Western blot on days 2 and 4 of culture. V=vehicle, T=trametinib 200 nM.

Accordingly, trametinib reduced MEK signaling in myeloid precursors differentiated with Brpkp110 conditioned media (FIG. 6F). Taken together, these results indicate that trametinib, by inhibiting the Ras-MAPK pathway in myeloid precursors, selectively decreases the accumulation of immunosuppressive Ly6C+ MDSCs, both at tumor beds and systemically. Thus, despite direct suppressive effects on T cells, trametinib, overall, enhances protective immunity by decreasing monocytic MDSCs, so that its full anti-tumor efficacy paradoxically requires CD8 T cells.

Figure 7A:
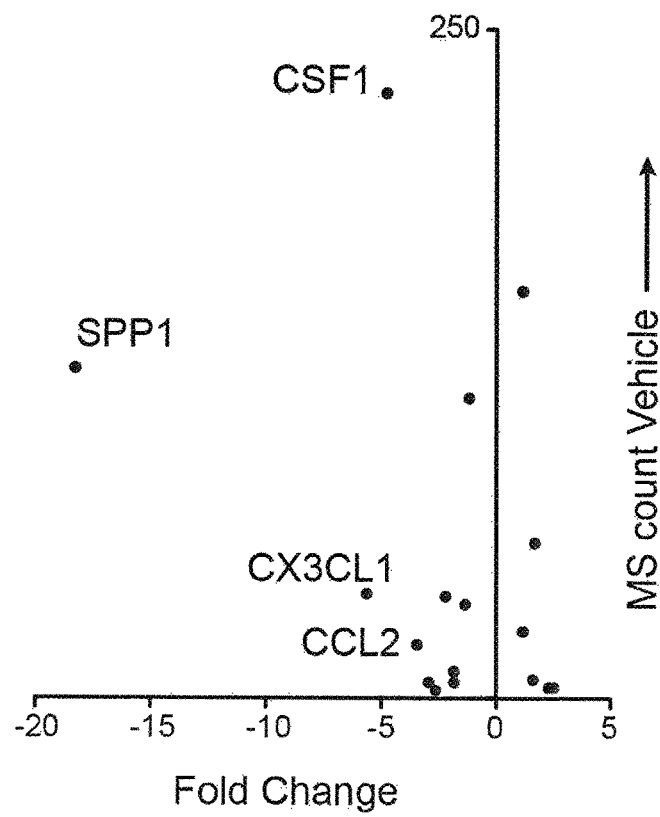
FIG. 7A illustrates that osteopontin chemoattracts MDSCs and is reduced by trametinib treatment of tumor cells. LC-MS/MS data are shown from supernatants of Brpkp110 cells cultured for 40 hrs in vehicle or 200 nM trametinib. Y axis=MS count (abundance) in vehicle supernatants. X axis=fold change. Positive values=(trametinib/vehicle), negative values=−(vehicle/trametinib).
Figure 7B:
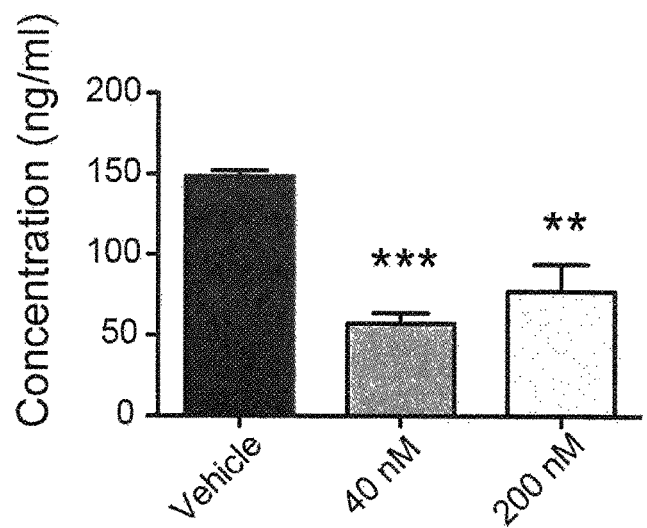
FIG. 7B shows osteopontin concentration measured from supernatants of Brpkp110 cells cultured overnight in the indicated conditions.

EXAMPLE 7: Trametinib Abrogates the Production of Osteopontin by KRas-Mutated Tumor Cells Our results indicated that trametinib impairs tumor progression by inhibiting myeloid cell mobilization, despite direct (IL-15-reversible) suppressive effects on lymphocytes. In addition, we hypothesized that trametinib may also alter the composition of the tumor microenvironment by modulating the KRas-dependent secretion of inflammatory factors by tumor cells. Correspondingly, LC-MS/MS analysis of culture supernatants from Brpkp110 cells revealed multiple cytokines dramatically altered in response to trametinib treatment. A number of factors known to be involved in recruitment of myeloid cells such as CSF1, CCL2, and CX3CL1 (FIG. 7A) were decreased after trametinib treatment. Most importantly, osteopontin (SPP1) was decreased >18-fold upon trametinib treatment, which was confirmed by ELISA in independent experiments (FIG. 7B). We focused on osteopontin because it has been reported to induce the expansion of MDSCs[12] and the recruitment of macrophages into the tumor[11].

Figure 7C:
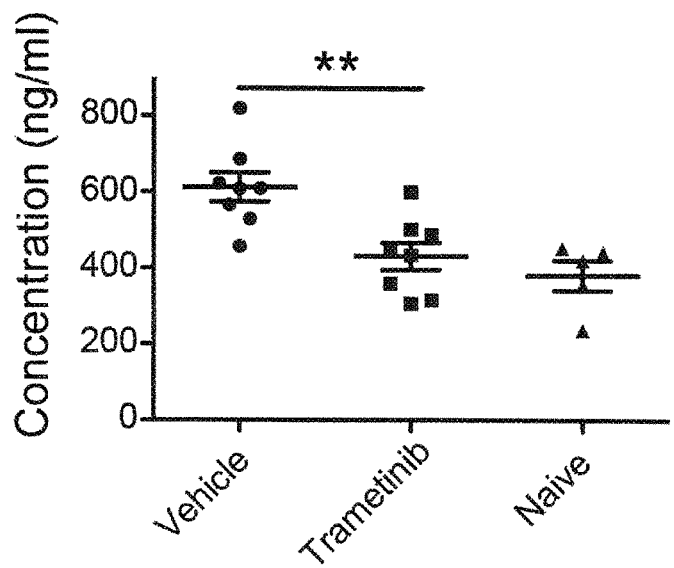
FIG. 7C shows osteopontin concentration from plasma samples collected from Brpkp110-bearing mice (or naïve tumor-free mice) gavaged with trametinib on days 7-9, and harvested on day 10.
Figure 7D:
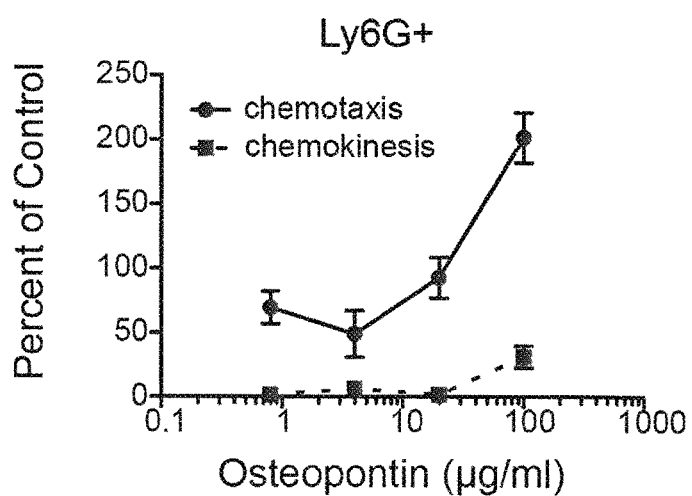
FIG. 7D shows that GM-CSF and IL-6 in vitro derived MDSCs were separated with Ly6G-MACS microbeads into Ly6G$^+$ and Ly6G$^-$ populations and assayed for their ability to migrate in a transwell assay towards osteopontin (chemotaxis) or within the presence of osteopontin (chemokinesis). *p<0.05, p<0.01, *p<0.001, unpaired t test.
Figure 7E:
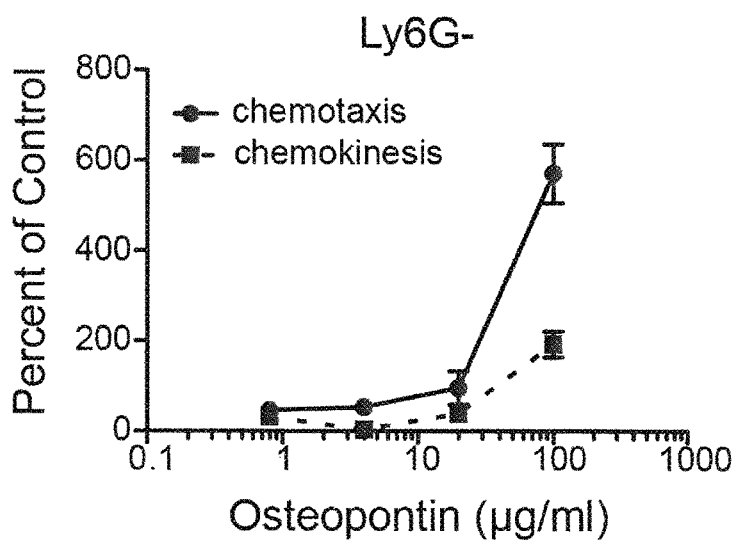
FIG. 7E shows that GM-CSF and IL-6 in vitro derived MDSCs were separated with Ly6G-MACS microbeads into Ly6G$^+$ and Ly6G$^-$ populations and assayed for their ability to migrate in a transwell assay towards osteopontin (chemotaxis) or within the presence of osteopontin (chemokinesis). *p<0.05, p<0.01, *p<0.001, unpaired t test.
Figure 12:
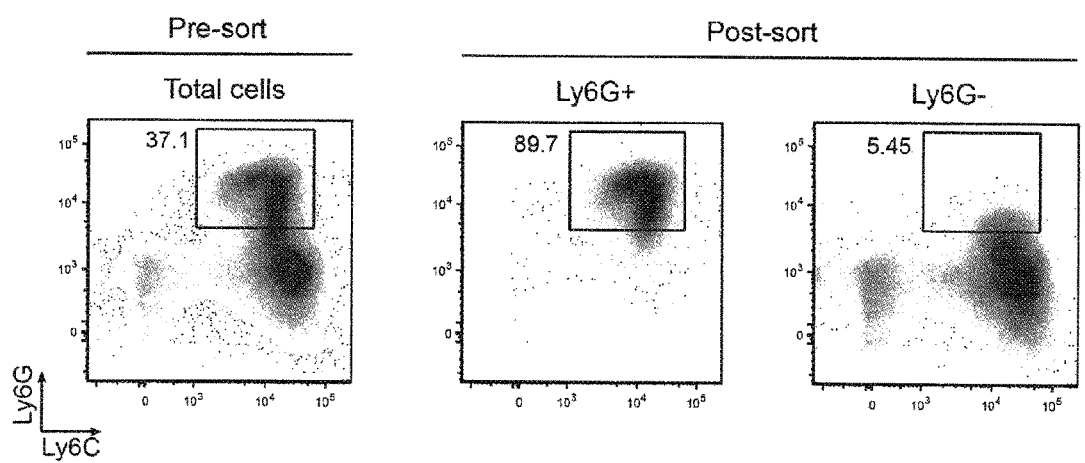
FIG. 12 illustrates that isolation of Ly6G$^+$ and Ly6G$^-$ bone marrow-derived MDSCs. GM-CSF and IL-6 in vitro derived MDSCs were separated with Ly6G-MACS microbeads into Ly6G$^+$ and Ly6G$^-$ populations. Pre- and post-sort cell populations were analyzed for Ly6G and Ly6C expression by flow cytometry.

Supporting the relevance of our proteomic analysis, the tumor-driven increase of osteopontin in plasma was abrogated by short-term (3 day) treatment with trametinib in Brpkp110-bearing mice (FIG. 7C). Importantly, when in vitro-derived Ly6G+ and Ly6G– MDSCs were isolated with Ly6G-MACS separation (FIG. 12), they were able to migrate towards a gradient of recombinant osteopontin (FIGS. 7D and 7E). This attraction was genuine chemotaxis because the migration of cells was greatly diminished when osteopontin was supplied on the same side of the transwell chamber as the cells. Together, these results indicate that trametinib also reduces MDSCs in the tumor by reducing the production of chemotactic cytokines by tumor cells through a direct anti-inflammatory effect that is independent of changes in the tumor cell cycle.

Summary

The most surprising result observed in these examples is that the in vivo effects of the MEK inhibitor trametinib are, at least in some tumors, independent from direct cytotoxic or cytostatic effects on cancer cells. These data offer a mechanistic explanation to the apparent inconsistency between in vitro and in vivo function of trametinib on anti-tumor immunity. Because many cells utilize MEK signaling, it is expected that trametinib would affect a diversity of cells. We show that trametinib reduces the accumulation of a major immunosuppressive cell population. This compensates for the direct inhibitory effects of trametinib on T cells, ultimately resulting in CD8 T cells being paradoxically required for the full efficacy of trametinib in our KRas-driven tumor model. In addition, direct T cell suppression by MEK inhibitors can be effectively overcome by some common gamma chain family cytokines such as IL-2, IL-7 and, especially, IL-15. In fact, the presence of these cytokines endogenously may explain the relatively mild suppressive effects of trametinib in vivo as compared to in culture. For instance, Hu-Lieskovan, et al recently found that trametinib synergized with an adoptive transfer immune therapy that included high-dose IL-2[7] in a mouse BRAF-driven tumor model. Our results suggest that any trametinib-driven T cell inhibition in this model may have been rescued by IL-2 administration. Nevertheless, as MEK inhibitors are being clinically tested against multiple KRas-driven malignancies[34-36], the data of these examples also provide a mechanistic rationale for therapeutic combination of trametinib with cytokine-based immune therapies, especially IL-15 agonists.

Our findings also highlight the importance of tumor microenviromental and systemic responses to trametinib. The finding that a tumor cell line (LLC) is sensitive to trametinib when grown in one location (subcutaneous) but resistant when grown in another (intraperitoneal) shows that the biological activity of trametinib is context dependent. The microenvironment-dependent effects of trametinib are also demonstrated by our data showing that trametinib has little impact on the proliferation of KRas-driven cells, but reduces their secretion of pro-inflammatory cytokines. Notably, trametinib decreases osteopontin secretion, which correlates with a decrease in monocytic MDSCs.

In their seminal study, Hu-Lieskovan, et al also looked at the proportions of MDSCs in tumors and spleens of mice treated with trametinib. They did not observe a decrease in monocytic Ly6C+ MDSCs and instead found a decrease in granulocytic Ly6G+ MDSCs in tumors of mice treated with trametinib and dabrafenib[7]. This difference might be due to the different treatment schemes. In their experiments trametinib was combined with either dabrafenib or adoptive cell therapy and it was not tested as a single agent as it was in our study. Also, their study used a BRAF-driven melanoma tumor, which may respond differently than our KRas-driven breast tumor in the secretion of inflammatory mediators under MEK inhibition.

Importantly, we found that the synergy between PI3K and MEK inhibitors on tumor cells[37] also exists for human T cells. These data suggest that combinatorial therapies in patients may compromise anti-tumor immunity, especially considering that combination treatment prevents the rescue by IL-15 in vitro. As treatments combining MEK inhibitors with other inhibitors are being investigated clinically[35], such treatments may also benefit from co-administration with a suitable cytokine/agonist as described herein.

Each and every patent, patent application, and publication, including websites cited throughout the disclosure, is expressly incorporated herein by reference in its entirety. While this invention has been disclosed with reference to specific embodiments, it is apparent that other embodiments and variations of this invention are devised by others skilled in the art without departing from the true spirit and scope of the invention. The appended claims include such embodiments and equivalent variations.

REFERENCES

1. Vesely M D et al, Natural innate and adaptive immunity to cancer. Annu Rev Immunol. 2011; 29:235-71.

2. Smith-Garvin J E, et al. T cell activation. Annu Rev Immunol. 2009; 27:591-619.
3. Miranda M B, Johnson D E. Signal transduction pathways that contribute to myeloid differentiation. Leukemia. 2007; 21:1363-77.
4. Yamaguchi T, et al. Suppressive effect of an orally active MEK1/2 inhibitor in two different animal models for rheumatoid arthritis: a comparison with leflunomide. Inflamm Res. 2012; 61:445-54.
5. Vella L J, et al. MEK inhibition, alone or in combination with BRAF inhibition, affects multiple functions of isolated normal human lymphocytes and dendritic cells. Cancer Immunol Res. 2014; 2:351-60.
6. Boni A, et al. Selective BRAFV600E inhibition enhances T-cell recognition of melanoma without affecting lymphocyte function. Cancer Res. 2010; 70:5213-9.
7. Hu-Lieskovan S, et al. Improved antitumor activity of immunotherapy with BRAF and MEK inhibitors in BRAF(V600E) melanoma. Sci Transl Med. 2015; 7:279ra41.
8. Liu L, T, et al. The BRAF and MEK Inhibitors Dabrafenib and Trametinib: Effects on Immune Function and in Combination with Immunomodulatory Antibodies Targeting PD-1, PD-L1, and CTLA-4. Clin Cancer Res. 2015; 21:1639-51.
9. Kono M, et al. Role of the mitogen-activated protein kinase signaling pathway in the regulation of human melanocytic antigen expression. Mol Cancer Res. 2006; 4:779-92.
10. Giachelli C M, et al. Evidence for a role of osteopontin in macrophage infiltration in response to pathological stimuli in vivo. Am J Pathol. 1998; 152:353-8.
11. Lin C N, et. al. The significance of the co-existence of osteopontin and tumor-associated macrophages in gastric cancer progression. BMC Cancer. 2015; 15:128.
12. Kim E K, et al. Tumor-derived osteopontin suppresses antitumor immunity by promoting extramedullary myelopoiesis. Cancer Res. 2014; 74:6705-16.
13. Gao N, et al. G1 cell cycle progression and the expression of G1 cyclins are regulated by PI3K/AKT/mTOR/p70S6K1 signaling in human ovarian cancer cells. Am J Physiol Cell Physiol. 2004; 287:C281-91.
14. Hou J Y, et al. Exploiting MEK inhibitor-mediated activation of ERalpha for therapeutic intervention in ER-positive ovarian carcinoma. PLoS One. 2013; 8:e54103.
15. Maus M V, et al. Ex vivo expansion of polyclonal and antigen-specific cytotoxic T lymphocytes by artificial APCs expressing ligands for the T-cell receptor, CD28 and 4-1BB. Nat Biotechnol. 2002; 20:143-8.
16. Stephen T L, et al. Transforming Growth Factor beta-Mediated Suppression of Antitumor T Cells Requires FoxP1 Transcription Factor Expression. Immunity. 2014; 41:427-39.
17. Scarlett U K, et al. Ovarian cancer progression is controlled by phenotypic changes in dendritic cells. J Exp Med. 2012; 209:495-506.
18. Law J H, et al. Phosphorylated insulin-like growth factor-i/insulin receptor is present in all breast cancer subtypes and is related to poor survival. Cancer Res. 2008; 68:10238-46.
19. Waldmann T A. The biology of interleukin-2 and interleukin-15: implications for cancer therapy and vaccine design. Nat Rev Immunol. 2006; 6:595-601.
20. Liao W, Interleukin-2 at the crossroads of effector responses, tolerance, and immunotherapy. Immunity. 2013; 38:13-25.
21. Budagian V, et al. IL-15/IL-15 receptor biology: a guided tour through an expanding universe. Cytokine Growth Factor Rev. 2006; 17:259-80.
22. Ueda Y, et al. Protein kinase C activates the MEK-ERK pathway in a manner independent of Ras and dependent on Raf. J Biol Chem. 1996; 271:23512-9.
23. Cantley L C. The phosphoinositide 3-kinase pathway. Science. 2002; 296:1655-7.
24. Xu W, et al. Efficacy and mechanism-of-action of a novel superagonist interleukin-15: interleukin-15 receptor alphaSu/Fc fusion complex in syngeneic murine models of multiple myeloma. Cancer Res. 2013; 73:3075-86.
25. Huarte E, et al. Depletion of dendritic cells delays ovarian cancer progression by boosting antitumor immunity. Cancer Res. 2008; 68:7684-91.
26. Nesbeth Y C, et al. CD4+ T cells elicit host immune responses to MHC class II-ovarian cancer through CCL5 secretion and CD40-mediated licensing of dendritic cells. J Immunol. 2010; 184:5654-62.
27. Rutkowski M R, et al. Initiation of metastatic breast carcinoma by targeting of the ductal epithelium with adenovirus-cre: a novel transgenic mouse model of breast cancer. J Vis Exp. 2014.
28. Jackson E L, et al. Analysis of lung tumor initiation and progression using conditional expression of oncogenic K-ras. Genes Dev. 2001; 15:3243-8.
29. Jonkers J, et al. Synergistic tumor suppressor activity of BRCA2 and p53 in a conditional mouse model for breast cancer. Nat Genet. 2001; 29:418-25.
30. Wee S, et al. PI3K pathway activation mediates resistance to MEK inhibitors in KRAS mutant cancers. Cancer Res. 2009; 69:4286-93.
31. Mirzoeva O K, et al. Basal subtype and MAPK/ERK kinase (MEK)-phospho-inositide 3-kinase feedback signaling determine susceptibility of breast cancer cells to MEK inhibition. Cancer Res. 2009; 69:565-72.
32. Turke A B, et al. MEK inhibition leads to PI3K/AKT activation by relieving a negative feedback on ERBB receptors. Cancer Res. 2012; 72:3228-37.
33. Mango I, et al. Tumor-induced tolerance and immune suppression depend on the C/EBPbeta transcription factor. Immunity. 2010; 32:790-802.
34. Infante J R, et al. A phase 1b study of trametinib, an oral Mitogen-activated protein kinase kinase (MEK) inhibitor, in combination with gemcitabine in advanced solid tumours. Eur J Cancer. 2013; 49:2077-85.
35. Bedard P L, et al. A phase Ib dose-escalation study of the oral pan-PI3K inhibitor buparlisib (BKM120) in combination with the oral MEK1/2 inhibitor trametinib (GSK1120212) in patients with selected advanced solid tumors. Clin Cancer Res. 2015; 21:730-8.
36. Blumenschein G R, Jr., et al. A randomized phase II study of the MEK1/MEK2 inhibitor trametinib (GSK1120212) compared with docetaxel in KRAS-mutant advanced non-small-cell lung cancer (NSCLC) dagger. Ann Oncol. 2015; 26:894-901.
37. Engelman J A, et al. Effective use of PI3K and MEK inhibitors to treat mutant Kras G12D and PIK3CA H1047R murine lung cancers. Nat Med. 2008; 14:1351-6.
38. Rutkowski M R, et al. Microbially driven TLR5-dependent signaling governs distal malignant progression through tumor-promoting inflammation. Cancer Cell. 2015; 27:27-40.

39. Roby K F, et al. Development of a syngeneic mouse model for events related to ovarian cancer. Carcinogenesis. 2000; 21:585-91.
40. Conejo-Garcia J R, et al. Tumor-infiltrating dendritic cell precursors recruited by a beta-defensin contribute to vasculogenesis under the influence of Vegf-A. Nat Med. 2004; 10:950-8.
41. Huarte E, et al. PILAR is a novel modulator of human T-cell expansion. Blood. 2008; 112:1259-68.
42. Cox J, Mann M. MaxQuant enables high peptide identification rates, individualized p.p.b.-range mass accuracies and proteome-wide protein quantification. Nat Biotechnol. 2008; 26:1367-72.
43. Wu, J, "IL-15 Agonists: The Cancer Cure Cytokine. J. Mol. Genet. Med., 2014 February, 7:85
44. Scarlett U K, et al, In situ stimulation of CD40 and Toll-like receptor 3 transforms ovarian cancer-infiltrating dendritic cells from immunosuppressive to immunostimulatory cells. Cancer Res. 2009 Sep. 15; 69(18):7329-37.
45. Zhu X et al, Novel Human Interleukin-15 Agonists, J Immunol 2009 August, 183:3598-3607

The invention claimed is:

1. A method of treating a mammalian subject having cancer or tumor cells comprising:
    (a) administering to said subject trametinib or GDC0973; and
    (b) administering to said subject interleukin-15 (IL-15) or interleukin-7 (IL-7) or an IL-15 agonist,
    wherein the agonist is selected from
        i. a complex of IL-15 with an α subunit of soluble IL-15 receptor (IL-15R);
        ii. the partial or whole sequence of soluble IL-15R;
        iii. an IL-15:IL-15Rα-Fc complex;
        iv. a hyperagonist IL-15-sIL-15Rα-sushi fusion protein;
        v. a triple fusion protein combining Apolipoprotein A-I, IL-15 and 15Rα-sushi;
        vi. a fusion protein of human IL-15 mutant IL-15N72D with the soluble domain of IL-15Rα; or
        vii. ALT-803
    wherein the combination of (a) and (b) reduce the proliferation of said cancer or tumor cells in vivo.

2. The method according to claim 1, wherein said cancer is a metastatic or refractory cancer.

3. The method according to claim 1, wherein said tumor is a refractory tumor or said tumor cells are refractory tumor cells or tumor cells with a Kras mutation.

4. The method according to claim 1, wherein the administration of (a) occurs before the administration of (b).

5. The method according to claim 1, wherein the administration of (a) occurs after the administration of (b).

6. The method according to claim 1, wherein the administration of (a) occurs substantially simultaneously with the administration of (b).

7. The method according to claim 1, further comprising administering repeated doses of one or more of component (a) or component (b) to the subject.

* * * * *